United States Patent
Feuerbach et al.

(10) Patent No.: US 9,828,642 B2
(45) Date of Patent: Nov. 28, 2017

(54) BIOMARKERS PREDICTIVE OF RESPONSIVENESS TO ALPHA 7 NICOTINIC ACETYLCHOLINE RECEPTOR ACTIVATOR TREATMENT

(71) Applicant: Novartis AG, Basel (CH)

(72) Inventors: Dominik Feuerbach, Basel (CH);
Baltazar Gomez-Mancilla, Basel (CH);
Yunsheng He, Cambridge, MA (US);
Donald Johns, Cambridge, MA (US);
Cristina Lopez-Lopez, Basel (CH);
Kevin Hall McAllister, Basel (CH);
Nicole Pezous, Basel (CH); Lisa Sandford, Basel (CH); Markus Weiss, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/735,288

(22) Filed: Jun. 10, 2015

(65) Prior Publication Data

US 2015/0275303 A1    Oct. 1, 2015

Related U.S. Application Data

(63) Continuation of application No. PCT/IB2013/060744, filed on Dec. 9, 2013.

(60) Provisional application No. 61/735,720, filed on Dec. 11, 2012.

(51) Int. Cl.

| | |
|---|---|
| *G01N 33/48* | (2006.01) |
| *C12Q 1/68* | (2006.01) |
| *A61K 45/06* | (2006.01) |
| *A61K 9/20* | (2006.01) |
| *A61K 31/444* | (2006.01) |
| *A61K 31/439* | (2006.01) |
| *A61K 9/16* | (2006.01) |
| *A61K 9/48* | (2006.01) |

(52) U.S. Cl.
CPC .......... *C12Q 1/6883* (2013.01); *A61K 9/2018* (2013.01); *A61K 9/2054* (2013.01); *A61K 9/2059* (2013.01); *A61K 9/2086* (2013.01); *A61K 31/439* (2013.01); *A61K 31/444* (2013.01); *A61K 45/06* (2013.01); *A61K 9/1623* (2013.01); *A61K 9/1652* (2013.01); *A61K 9/4858* (2013.01); *A61K 9/4866* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

FOREIGN PATENT DOCUMENTS

| WO | 2004022556 A1 | 3/2004 |
|---|---|---|
| WO | 2010056622 A1 | 5/2010 |
| WO | 2010085724 A1 | 7/2010 |

OTHER PUBLICATIONS

Office Action and English Translation thereof for Korean Patent Application No. 10-2015-7015933 dated Oct. 20, 2016, 16 pages.
Office Action for Chinese Patent Application No. 201380064603.1 dated Jul. 29, 2016, 16 pages.
Abnet et al., "The influence of genetic polymorphisms in Ahr, CYP1A1, CYP1A2, CYP1B1, GST M1, GST T1 and UGT1A1 on urine 1-hydroxypyrene glucuronide concentrations in healthy subjects from Rio Grande do Sul, Brazil," Carcinogenesis. 28(1):112-7 (2007).
Ayari et al., "Role of CYP1A2 polymorphisms in breast cancer risk in women," Mol Med Rep. 7(1):280-6 (2013).
Chang et al., "Prevalence in the United States of selected candidate gene variants: Third National Health and Nutrition Examination Survey, 1991-1994," Am J Epidemiol. 169(1):54-66 (2009).
Klemm et al., "Development of a high throughput single nucleotide polymorphism screening method for the cytochrome P450 1A2 polymorphisms CYP1A2*1C and CYP1A2*1F: are they useful as predictive markers in mental disorders?" Clin Lab. 56(9-10):473-80 (2010).
Meyer et al., "3-[2,4-Dimethoxybenzylidene]anabaseine (DMXB) selectively activates rat alpha7 receptors and improves memory-related behaviors in a mecamylamine-sensitive manner," Brain Res. 768(1-2):49-56 (1997).
Song et al., "Effect of CYP1A2 polymorphism on the pharmacokinetics of agomelatine in Chinese healthy male volunteers," J Clin Pharm Ther. 39(2):204-9 (2014).
Tay et al., "Functional polymorphisms of the cytochrome P450 1A2 (CYP1A2) gene and prolonged QTc interval in schizophrenia," Prog Neuropsychopharmacol Biol Psychiatry. 31(6):1297-302 (2007).
Tietje et al., "Preclinical characterization of A-582941: a novel alpha7 neuronal nicotinic receptor agonist with broad spectrum cognition-enhancing properties," CNS Neurosci Ther. 14(1):65-82 (2008).
International Search Report and Written Opinion for PCT/IB2013/060744, dated May 26, 2014, (16 pages).

*Primary Examiner* — Larry D Riggs, II
(74) *Attorney, Agent, or Firm* — Hoffman Warnick LLC

(57) ABSTRACT

The invention provides methods for predicting therapeutic responsiveness of a subject suffering from cognitive impairments or dysfunctions, psychotic and/or neurodegenerative disorders to an alpha 7 nicotinic acetylcholine receptor activator treatment.

11 Claims, No Drawings

SEQUENCE LISTING

```
<160> NUMBER OF SEQ ID NOS: 3

<210> SEQ ID NO 1
<211> LENGTH: 1001
<212> TYPE: DNA
<213> ORGANISM: Homo sapiens

<400> SEQUENCE: 1
cgaattgtaa caaatatatt acaccactgc aagatgttaa taatagggga aactgcagag      60
tgggggtggt aaatggccac ttttacctcc ctcatcatac tttccactca atttttctgt     120
gaaccaaaga ctgctctaaa aaaatctatt agcttttaa aattccttgg ctcccctcca     180
aaaagtgtac atatgacatg atctcattta tgtaaaatac aacaagcaaa acaaatccat     240
gcaatagatg ttggggtcat gggtacccct gagaaaggaa cacaacggga cttcttggat     300
gcttatgatg tctcttgatt agagctggtt atatgtgtgt ttgttaagtt tgcaaaaatt     360
catcaagcta cacatgatcg agctatacat gacatatgca cttttccatt tatttattta     420
tttttgagac agaatcttgc tctgtcaccc aggctggagt gcagtggtgc gatcttggct     480
caccgcaacc tccgcctctc agattcaagc aattgtcatg ccccagcttc ccgagtagct     540
ggaattacag gtgtgcacca tcacgcccag ctaatttttt tttgtatttt tagtagagat     600
gaggtttcac tatgttggcc aggctggtct tgaactcctg gcctcactca agtgatcctc     660
```

```
ccacctcggc tcccaaagt gctagaatta caggtgtgag tcaccggtcc cagctgacat    720
atgcactttt ctatattgta tcctgtaatt taatttttt aagttttaag aaaacattaa    780
aaataaaaag ataaatagtc tgtcatacag gagaatttca aatagtttat ggagataatc    840 cccctcaag gagaaggagc gtaatccccc actccttcgg tgtgggctgt gcatagtgac    900
ttccttccaa aaggtacagt atggaaaggt gggaaggag taactttaca gtgaagagac    960
ctgacacgca ctaccttagc caggtgatca aggtcaacat c                      1001
```

```
<210> SEQ ID NO 2
<211> LENGTH: 1001
<212> TYPE: DNA
<213> ORGANISM: Homo sapiens

<400> SEQUENCE: 2
cgaattgtaa caaatatatt acaccactgc aagatgttaa aataggggga aactgcagag     60
tgggggtggt aaatggccac ttttacctcc ctcatcatac tttccactca attttctgt    120 gaaccaaaga ctgctctaaa aaatctatt agcttttta aattccttgg ctcccctcca    180
aaaagtgtac atatgacatg atctcattta tgtaaaatac aacaagcaaa acaaatccat    240
gcaatagatg ttgggtcat gggtacccct gagaaaggaa cacaacggga cttcttggat    300
gcttatgatg tctcttgatt agagctggtt atatgtgtgt tgttaagtt tgcaaaaatt    360 catcaagcta cacatgatcg agctatacat gacatatgca cttttccatt tatttattta    420
tttttgagac agaatcttgc tctgtcaccc aggctggagt gcagtggtgc gatcttggct    480
caccgcaacc tccgcctctc ggattcaagc aattgtcatg ccccagcttc ccgagtagct    540
ggaattacag gtgtgcacca tcacgcccag ctaattttt tttgtatttt tagtagagat    600
gaggtttcac tatgttggcc aggctggtct tgaactcctg gcctcactca agtgatcctc    660
ccacctcggc tcccaaagt gctagaatta caggtgtgag tcaccggtcc cagctgacat    720
atgcactttt ctatattgta tcctgtaatt taatttttt aagttttaag aaaacattaa    780
aaataaaaag ataaatagtc tgtcatacag gagaatttca aatagtttat ggagataatc    840 cccctcaag gagaaggagc gtaatccccc actccttcgg tgtgggctgt gcatagtgac    900
ttccttccaa aaggtacagt atggaaaggt gggaaggag taactttaca gtgaagagac    960
ctgacacgca ctaccttagc caggtgatca aggtcaacat c                      1001
```

```
<210> SEQ ID NO 3
<211> LENGTH: 7758
<212> TYPE: DNA
<213> ORGANISM: Homo sapiens

<400> SEQUENCE: 3
gaagctccac accagccatt acaaccctgc caatctcaag cacctgcctc tacaggtacc     60
tttcttggga ccaatttaca atctctggga tccccaacta tagaacctgg aagctagtgg    120
ggacagaaag acggggagcc tgggctaggt gtaggggtcc tgagttccgg gctttgctac    180
ccagctcttg acttctgttt cccgattta aatgagcagt ttggactaag ccatttttaa    240
ggagagcgat ggggagggct tcccccttag cacaagggca gccctggccc tggctgaagc    300
ccaaccccaa cctccaagac tgtgagagga tggggactca tccctggagg aggtgcccct    360
cctggtattg ataaagaatg ccctggggag ggggcatcac aggctatttg aaccagccct    420
gggaccttgg ccacctcagt gtcactgggt aggggggaact cctggtccct tgggtatatg    480
gaaggtatca gcagaaagcc agcactggca gggactcttt ggtacaatac ccagcatgca    540
```

```
tgctgtgcca ggggctgaca agggtgctgt ccttggcttc ccatttttgg agtggtcact      600
tgcctctact ccagccccag aagtggaaac tgagatgatg tgtggaggag agagccagcg      660
ttcatgttgg gaatcttgag gctcctttcc agctctcaga ttctgtgatg ctcaaagggt      720
gagctctgtg ggcccaggac gcatggtaga tggagcttag tctttctggt atccagctgg      780
gagccaagca cagaacacgc atcagtgttt atcaaatgac tgaggaaatg aatgaatgaa      840
tgtctccatc tcaaccctca gcctggtccc tcctttttc cctgcagttg gtacagatgg       900
cattgtccca gtctgttccc ttctcggcca cagagcttct cctggcctct gccatcttct      960
gcctggtatt ctgggtgctc aagggtttga ggcctcgggt ccccaaaggc ctgaaaagtc     1020
caccagagcc atggggctgg cccttgctcg gcatgtgct gaccctgggg aagaacccgc      1080
acctggcact gtcaaggatg agccagcgct acggggacgt cctgcagatc cgcattggct     1140
ccacgcccgt gctggtgctg agccgcctgg acaccatccg gcaggccctg gtgcggcagg     1200
gcgacgattt caagggccgg cctgacctct acacctccac cctcatcact gatggccaga     1260
gcttgacctt cagcacagac tctggaccgg tgtgggctgc ccgccggcgc ctggcccaga     1320
atgccctcaa caccttctcc atcgcctctg acccagcttc ctcatcctcc tgctacctgg     1380
aggagcatgt gagcaaggag gctaaggccc tgatcagcag gttgcaggag ctgatggcag     1440
ggcctgggca cttcgaccct tacaatcagg tggtggtgtc agtggccaac gtcattggtg     1500
ccatgtgctt cggacagcac ttccctgaga gtagcgatga gatgctcagc ctcgtgaaga     1560
acactcatga gttcgtggag actgcctcct ccgggaaccc cctggacttc ttccccatcc     1620
ttcgctacct gcctaaccct gccctgcaga ggttcaaggc cttcaaccag aggttcctgt     1680
ggttcctgca gaaaacagtc caggagcact atcaggactt tgacaaggtg agcccggggt     1740
gcaggtggca aggggcacct tgcagggcct gggtgcagcc cctccctccc agctccagca     1800
tgcccacaca gctgctgtgt tgccaaggcc taggaaggct ctggacacct cagaccagct     1860
gtgtgacctg gagccgactc ttccccttct ctgggcctca gtttcctcat ccttgaagcc     1920
cccttctcag ggctcctcaa agcccccaag aaaaaagccc tggaaatggg gccctagcag     1980
agtcctgcaa tgtgggggc ctatgagtga aaagctttc attctgcaga aacctaaacc      2040
ccaacagagg ctaatcccca gctctggtgt cacgttgctt ccctgtgttc acactaacct     2100
tttccttctt tgaaattgga ccctggtgt tattgggagg aagggtcaat ggggcataaa      2160
atgacacttt aagccatacc cagggctgct accagctcct gctgcaagct gcaaccccct     2220
gcctagagac caagttggga ggatagggg gtacccagcc accaggtaca ggccagggga      2280
gtggagcaac gttcagcctt tgaccttgga agtgccagag gtgcccctaa gcttgtgccc     2340
cctcagaaca gtgtccggga catcacgggt gccctgttca agcacagcaa gaagggggcct    2400
agagccagcg gcaacctcat cccacaggag aagattgtca accttgtcaa tgacatcttt     2460
ggagcaggta ggaaccagaa ccttgcccct ccatccaaca atgcctgctg ttcacccaca     2520
gccttgccca gcccctcagt ccatgaaata acccaccaac cctacaccag atggtacaac     2580
atactgagat ctggcttggg atcagggttt gagcctgggc tatgccacca attcccagtg     2640
gagaaacagc aaagtccttc tcctccccta ggcttcagtt tccccatctg aacaataagg     2700
tgttctctgg cctgtaagtc taggccccta taattccagc agctaattct gaaacctgta     2760
tctcaagttt atgttgaaga gacccagcct ctgtcttcag gaaactcaca ggctagggcc     2820
agagaaagct aatgctggat acatacatag cagatacttg ggaaatgatg gtttccttgt     2880
```

```
ttctgtcttc cttctttcct caccttacac tacacggttc aggatttgac acagtcacca    2940
cagccatctc ctggagcctc atgtaccttg tgaccaagcc tgagatacag aggaagatcc    3000
agaaggagct gggtacatgg gggcccccaa ccctatagcc aggagaagcc ttgagaccca    3060
ggttgtttgt tcagtctaca aacacctgtt atgtgcctgc tgtgtgcaag ccctgggcac    3120
acagtagtgc ctgcccttgc ctagaagatg tgggaggtta gtgggtcgc agacttgtga     3180
atagacagtc ttacataaga gtgacatggg gtataagagg ggataattca tggggcagtt    3240
agggcagccc ctgagctctg cttgtcctct gtgttctaca gacactgtga ttggcaggga    3300
gcggcggccc cggctctctg acagacccca gctgccctac ttggaggcct tcatcctgga    3360
gaccttccga cactcctcct tcttgccctt caccatcccc cacaggtgag gcctgccggt    3420
tctgccctcc cacctctaaa gtgcttgcca tgttttctct tcctggcttc tcagccctgg    3480
ccctggctca gcatctcctt cccgacctcg ttccccacag atcccggcct cagtctgccc    3540
ccatccagtc caaacataat ctaacccccca gctctcagga gaaagttcca cttgtgatct    3600
cagcgctcat tcccctctgt tcatattccc tccctcccag tgccctctgt gccagtcagg    3660
tcggcctcac cctcacaagc atgacccctat tggcctccaa tcttgctaac gctgaacctt    3720
ctgcctggaa taccttctag cctcttctct gaccaccaga atcctaccct tgctcaaagt    3780
caatgccgac acgagcttcc tctccccaga agcctttga ctcatccagc tggcacagct     3840
tcattcctga tgtcttatag gacttacagc catcagccct tgatcatgcc ctggaatttt    3900
aacaatgtca agagagttag tgagcattta cttctaccca aacgttgttc tagttattcc    3960
tgcagtaaga ggcctgaatc cccagccagg ctagaaattc cccggggctg ccccaggctg    4020
cctgctgctt ttttttttt tttttttttt tcatagaaa atagaaaaac atttatctga      4080
aattgcctgc ttcttggctc cagagaacag ccaagtgcgc agccaggcgc aaagagaagt    4140
ttagtaaata cttgctgaag ttaaagaaca ggacgcaagg aagagggagg atgtttctac    4200
ctcttccctg ttcctccccct cccctcccag tgtagggatg gagatggcgg tgggcaggct   4260
gtctggatgg ggtggaggta ggagcaacac atgccccagc tttccagccc tgagcctcac    4320
agtgccctct tccctcctca gcacaacaag ggacacaacg ctgaatggct tctacatccc    4380
caagaaatgc tgtgtcttcg taaaccagtg gcaggtcaac catgacccgt gagtacatac    4440
ccctcacgaa aaaatgtgtg caggttcagc agtcaggaag gctgtttgtc cctgctagga    4500
actgtttata taatgaaagg aggggacctc aattgctata gtctgctcta agtgacgata    4560
tttacaaaag tttcacaaac tttagtgcac aggaatcaac taggatggcc aggcgcagtg    4620
gctcaagcct ataatcccag cagtttggga ggccgaggca ggcagatcac ttgaggtcag    4680
gagtttgaga ccagcctggg caacatggtg aaacccatc tctactaaaa atacaaaaca    4740
aaaattagcc ggacatggtg gtgcgcctat aatcccagct actccagagg ctgaggcagg    4800
agaattgctt gaactctgga ggtagaggct gcagtgagcc gagatcgctc cactgcactc    4860
cagcctgggt gacggagtga gactctgcct caaaaaaaaa aaaaaaaat caaccaagac     4920
gtttgttaca ggtgatggtt cccccaggat tctactgtgg tatctaaggt ggggtacctc    4980
aggcgattct gatgtgaatg gctcagagac ctctctttgg aaagccccac tttagtgtat    5040
aggtaggggg accatatata taatttacca tccacactgg acatttgag tgtgaaaatg     5100
ctatcaatgt ttatgctagt catcattact ccaaaacaat aaacataagc caggacatac    5160
tgttgaggcc ccttaggagg catattttga gtaggatgaa gaaacgtatg tctttctttc    5220
ttcctttcac tttaattttt aaatagagac aaggtcttcc tatgtggtcc aggctggttt    5280
```

```
tgaactcctg ggttcaaggg atcttcctgc ctcagcctcc caaagtgcta gggttacggg      5340
tgtaagccac caaacccagc ctgttttct tcttttaatt tcttttagat aaagcattat       5400
ttaaagtaaa ttaatattaa aaggcactat ctttaaggct ggtcatttta gagagagctt      5460
tgtaaaagaa ataagcatca ggccaggtgt ggtgactcat gcctgtaacc ccagcacttt      5520
gggagtccga ggaaggtgga tcgcttgagc tcatgagtct gagaccagtg aaacccgtc       5580 tctgcaaaaa aaaaaaaaa aaaaatacaa aaaattagcc ggatatggtg cctgtagtcc       5640
cagctacacg ggaggctcag gtgggtggtt ggcttgagct ggggaggcag agagagtgca      5700
gtgagctgag atcgcaccac tgtactccag cctgggtgat aggagccgga gggtgtctca     5760
aaaaaaaaaa aagaaagaaa agaaaaagaa ataagcatca aagttcagtt tggttccttc     5820
ccacctaccc ttcattgctt tcaaagtgcc ctcacacttg tgttctcaac agaagtctcc    5880
ctcccccagg cacctcctcc cagggcctct ccagccctga ggtcccatct cctctgttcc    5940
tcttgcagag agctgtggga ggaccctct gagttccggc ctgagcggtt cctcaccgcc     6000
gatggcactg ccattaacaa gcccttgagt gagaagatga tgctgtttgg catgggcaag   6060
cgccggtgta tcggggaagt cctggccaag tgggagatct tcctcttcct ggccatcctg   6120
ctacagcaac tggagttcag cgtgccgccg ggcgtgaaag tcgacctgac ccccatctac    6180
gggctgacca tgaagcacgc ccgctgtgaa catgtccagg cgcggctgcg cttctccatc    6240
aactgaagaa gacaccacca ttctgaggcc agggagcgag tggggccag ccacggggac      6300 tcagcccttg tttctcttcc tttctttttt taaaaaatag cagctttagc caagtgcagg    6360
gcctgtaatc ccagcatttt aggaggccaa ggttggagga tcatttgagc ccaggaattg    6420
gaaagcagcc tggccaacat agtgggaccc tgtctctaca aaaaaaaat ttgccaagag     6480 cctgagtgac agagcaagac cccatctcaa aaaaaaaac aaacaaacaa aaaaaaacc      6540 atatatatac atatatatat agcagcttta tggagatata attcttatgc catataattc    6600
accttctttt ttttttttg tctgagacag aatctcagtc tgtcacccag gttggagtgc    6660
agtggcgtga tctcagctca ctgcaacctc cacctgcag gttcaagcaa tcctcccact      6720
tcagcctccc aagcacctgg gattacaagc atgagtcact acgcctggct gattttgta    6780 gttttagtgg agatgggtt tcaccatgtt ggccaggctt gtctcgaact cctgaccca     6840 agttatccac ctgccttggc ttcccaaagt cctgggatta caggtgtgag ccaccacatc   6900
cagcctaact tacattctta aagtgtcgaa tgacttctag tgtagaattg tgcaaccatc    6960
accagaatta attttattat tcttattatt tttgagacag agtcttactc tgttgccagg    7020
ctggagtgca gtggcgcgat ctcagctcac tacaacctcc gcctcccatg ttcaagcgat   7080
tctcctgcct cagcctccg agtagctggg actataggca tgcgccacca tggccagcta   7140 attttgtat ttttagtaga gacgaggttt cactgtgttg gccaggatgg tctccatctc    7200
ttgacctcgt gatccacccg cctcagcct ccaaagtgct gggattaaca ggtatgaacc     7260
accgcgccca gccttttgt ttttttttt tttgagacag agtcttcctc tgtctcctaa     7320
gctggagtgc agtggcatca tctcagctca ctgcaacctc tgcctcccag gttcaagtgc    7380
ttctccagcc tcagcctccc aagtagctga gactacagg acacaccacc acgcctggct    7440 aattttgta tttttagtag agacgggtt caccatgttg gctagactag tctcaaactc     7500
ctgacctcaa gtgatctgcc cgcctcgacc tctctcaaag tgctggcatt acaggtgtga    7560
gccacggtgc ccggcccaca attaatttta gaacattttc atcacccta aaagaaaccc    7620
```

```
tgcacccatt agcagtccct ccacatttcc ccctagcctg cctccccgc ctcaccagcc    7680 ctggcaactg ctaatctact ttctgtgtct atggatttgc cttctctaaa catttcatat    7740
aaatggaatt acacaatg                                                  7758
```

BIOMARKERS PREDICTIVE OF RESPONSIVENESS TO ALPHA 7 NICOTINIC ACETYLCHOLINE RECEPTOR ACTIVATOR TREATMENT

CROSS REFERENCE TO RELATED APPLICATIONS

The instant application is a continuation of co-pending International Patent Application No. PCT/IB2013/060744, filed Dec. 9, 2013, which claims the benefit of U.S. Provisional Application No. 61/735,720, filed Dec. 11, 2012. Each of the foregoing is incorporated in its entirety as though fully set forth herein.

SEQUENCE LISTING

The sequence listing contained in the electronic file titled "VAND-0148-U.S._SequenceListing_ST25.txt," created Jun. 10, 2015 and comprising 14 KB, is hereby incorporated herein by reference.

BACKGROUND OF THE INVENTION

Cognitive deficits have been recognized as a clinically significant aspect of schizophrenia and the major factor determining successful functional rehabilitation and social reintegration (Green, 1996; Green, 2007). A cognitive impairment in schizophrenia or in other mental disease is an acquired deficit in one or more of memory function, problem solving, orientation and/or abstraction that impinges on an individual's ability to function independently, particularly pronounced in verbal memory, executive functions, attention and vigilance, verbal fluency and motor speed, but also including other functions. Cognitive impairments are not the result of positive or negative symptoms of the disorder or accounted for by motivational deficits (Harvey et al, 2004). In most cases cognitive impairments do not worsen or improve with illness progression (Harvey et al, 2004; Hoff et al, 1999). There are no accepted treatments for cognitive deficits in schizophrenia. Currently available antipsychotic treatments do not improve cognition beyond practice effects (Goldberg et al, 2007; Keefe et al, 2007).

Several lines of evidence suggest that the alpha 7 nicotinic acetylcholine receptor (α7-nAChR) could be involved in cognitive dysfunctions in schizophrenia. A link between P50 sensory gating deficits displayed by schizophrenics and a defect on chromosome 15q14, the site of the α7-nAChR gene (Chini et al., 1994), was established by Freedman et al., 1997. Polymorphisms in the α7-nAChR promoter region that decreased transcription were more prevalent in schizophrenic patients than in the control subjects (Leonard et al., 2002). Postmortem studies have demonstrated that α7-nAChR levels are decreased in brains of schizophrenia patient's (Freedman et al., 1995). α7-nAChRs are expressed in key brain areas important for learning and memory (hippocampus, prefrontal cortex and amygdala). Activation of the α7-nAChR has been shown to modulate glutamatergic, GABAergic and cholinergic neurotransmitter release and to improve cognition in a variety of different pre-clinical animal models.

Novel α7-nAChR activators have been developed for the treatment of disease conditions associated with defective or malfunctioning nicotinic acetylcholine receptors. Although it has been assumed that α7-nAChR activator treatment might improve cognitive deficits controversial data and variation of individual cognitive responses to α7-nAChR activator treatments have so far hindered the development of α7-nAChR activator based treatments of cognitive impairments, e.g. it is not known why some patients do not respond to these medications. Consequently, there is a need to predict in advance of treatment whether a patient suffering from cognitive impairments or dysfunctions is likely to be responsive to treatment with an α7-nAChR activator. Accordingly, ways for predicting responsiveness to an α7-nAChR activator in patients with cognitive impairments or dysfunctions are urgently needed in the art.

SUMMARY OF THE INVENTION

There is a need to predict whether a patient is likely to be responsive to treatment with an α7-nAChR activator. This objective is achieved by the methods and compositions provided within this disclosure. In the present invention genetic variants of the chromosomal locus 15q24 have been surprisingly shown to be predictive markers for responsiveness of patients suffering from cognitive impairments or dysfunctions to α7-nAChR activator treatment.

A first subject matter of the disclosure therefore relates to a composition comprising an alpha 7 nicotinic acetylcholine receptor activator for treatment of cognitive impairments, psychotic and/or neurodegenerative disorders in a selected patient population, wherein the patient population is selected on the basis of having at least one indicative SNP of the human cytochrome P450, family 1, subfamily A, polypeptide 2 (CYP1A2) gene (SEQ ID NO. 3; chromosome 15 NC_000015.9, cytogenetic location: 15q24.1; genomic coordinates (GeneLoc): 75,041,184-75,048,941), Entrez Gene ID: 1544.

An indicative SNP, like rs2069514-A (SEQ ID NO. 1) as disclosed herein, is differentially present in human individuals and the likelihood of responsiveness of a patient can be predicted in the basis of the presence of the SNP rs2069514-A variant in the genome of said patient. Hence, an "indicative SNP" in the context of this application refers to a specific SNP that allows predicting in advance of treatment whether a patient suffering from cognitive impairments, psychotic and/or neurodegenerative disorders is likely to be responsive to treatment with an α7-nAChR activator. An indicative SNP in the context of this disclosure refers to a SNP present in the CYP1A2 gene and those forming a haplotype or in the same linkage disequilibrium with said SNPs.

In another embodiment, the disclosure relates to a method for the identification of indicative SNPs of the CYP1A2 gene comprising the steps of:

a) selecting a group of schizophrenic patients large enough to obtain statistically significant results; and
b) obtaining the genotype of said patients at the genetic locus of the CYP1A2; and
c) administering to said patients a therapeutic effective amount of an alpha 7 nicotinic acetylcholine receptor activator; and
d) performing an cognition assessment test with the patient of step c) by using a schizophrenic cognitive test battery (e.g. CogState™ schizophrenia Battery); and
e) subdivide the patients of step d) in responder and non-responder subgroups by identifying those patients showing statistically relevant improved visual learning, memory capabilities, improved cognitive function, improved reasoning, problem solving capabilities or improvements on attention and vigilance ("responders"), whereas the improvements, measured as effect size as described in the Example section below, are at least about 0.1, or about 0.2, or about 0.3, or about 0.4 or above about 0.5; and f) analyze the DNA sequence of the genetic loci of the responder and non-responder subpopulations identified in step e) and select those SNPs only present at the genetic loci of the CYP1A2 gene of the responders;

g) identify heterozygous or homozygous indicative SNP variants by correlating the existence of the SNPs selected in step f) with the results of the cognition test of step d).

Methods for obtaining and analyzing the genotype of a patient at a defined locus or gene as well as the cognition assessment test are well known in the art and described in detail herein.

Preferably, the mentioned composition is used to treat cognitive impairments, psychotic and/or neurodegenerative disorders in which alpha 7 nicotinic acetylcholine receptor activation plays a role or is implicated. In one embodiment the cognitive impairments, psychotic and/or neurodegenerative disorders are selected from the group consisting of mild cognitive impairment, Alzheimer's disease, Parkinson's disease dementia, dementia with Lewy Bodies, schizophrenia, vascular dementia, AIDS-dementia, senile dementia, mild cognitive impairment related to age (MCI), age associated memory impairment, autism, dementias in frontal lobe degenerations, stroke, basalganglia degenerative disorders, multiple sclerosis, trauma, brain tumors, brain infections, hydrocephalus, depression, toxic or metabolic disorders and drug induced dementias.

In another embodiment the composition is used in patient population selected on the basis of carrying the human CYP1A2 SNP rs2069514-A (SEQ ID No. 1) or the SNP rs2069514-G (SEQ ID NO. 2) or a SNP forming a haplotype together with said SNPs or a SNP in the same linkage disequilibrium with said SNPs.

In another embodiment, the composition for treatment of cognitive impairments, psychotic and/or neurodegenerative disorders is used in patients selected on the basis of being homozygous for the above mentioned indicative CYP1A2 SNP rs2069514-NA (SEQ ID NO. 1) or corresponding indicative CYP1A2 SNP haplotypes, or heterozygous for the indicative CYP1A2 SNP rs2069514-NG or corresponding indicative CYP1A2 SNP haplotypes.

Furthermore, the disclosure relates to compositions as described herein, and used for the inventive methods, comprising an alpha 7 nicotinic acetylcholine receptor activator of formula (I)

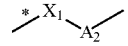

wherein $L_1$ is —$CH_2$—; $L_2$ is —$CH_2$— or —$CH_2$—$CH_2$—; and $L_3$ is —$CH_2$— or —$CH(CH_3)$—; or
$L_1$ is —$CH_2$—$CH_2$—; $L_2$ is —$CH_2$—; and $L_3$ is —$CH_2$—$CH_2$—;

$L_4$ is a group selected from

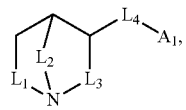

L4a

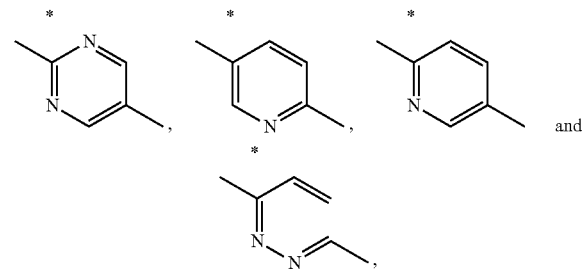

L4b wherein the bond marked with the asterisk is attached to the azabicycloalkyl moiety;

$R_1$ is hydrogen or $C_{1-4}$alkyl; $X_1$ is —O— or —NH—; $A_2$ is selected from

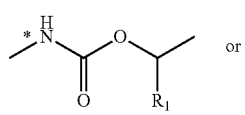

and wherein the bond marked with the asterisk is attached to $X_1$; $A_1$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_2$, and wherein a substituent on a nitrogen in a heterocyclic ring system may not be halogen; each $R_2$ independently is $C_{1-6}$alkyl, $C_{1-6}$halogenalkyl, $C_{1-6}$alkoxy, $C_{1-6}$ halogenalkoxy, halogen, cyano or a three- to six-membered monocyclic ring system which may be aromatic, saturated or partially saturated and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen; or two $R_2$ at adjacent ring atoms form a $C_{3-4}$alkylene group, wherein 1-2 carbon atoms may be replaced by $X_2$, and wherein the $C_{3-4}$alkylene group may be substituted once or more than once by $R_3$; each $X_2$ independently is —O— or —$N(R_4)$—; each $R_4$ independently is hydrogen or $C_{1-6}$alkyl; and each $R_3$ independently is halogen or $C_{1-6}$alkyl; in free base form or in acid addition salt form.

An additional subject matter of the disclosure relates to a composition as described herein, and used for the inventive methods, wherein the alpha 7 nicotinic acetylcholine receptor activator is used as free base or pharmaceutically acceptable acid addition salt form. In another embodiment, the alpha 7 nicotinic acetylcholine receptor activator is in its free base or pharmaceutically acceptable acid addition salt form, in association with a pharmaceutical carrier or a diluent.

In another embodiment of the disclosure, the composition as described herein, and used for the inventive methods, further comprises a second cognition enhancer or a therapeutic compound useful for the treatment of cognitive impairments, psychotic and/or neurodegenerative disorders. The second cognition enhancer or therapeutic compound may for example be a conventional antipsychotic or an atypical antipsychotic.

In yet another embodiment, the disclosure relates to a method for predicting therapeutic responsiveness of an individual or a group of individuals to alpha 7 nicotinic acetylcholine receptor activator treatment for increasing the cognitive skills and/or treatment of a cognitive impairment, psychotic and/or neurodegenerative disorder comprising the steps of: I) obtaining the genotype of the individual at the genetic locus of the CYP1A2 gene; II) identifying those individuals of step I) carrying the CYP1A2 SNP rs2069514-A (SEQ ID NO. 1) or the SNP rs2069514-G (SEQ ID NO. 2) or a SNP forming a haplotype with said SNPs, wherein homozygous presence of the CYP1A2 SNP rs2069514-NA or SNP haplotype, or heterozygous presence of the CYP1A2 SNP rs2069514-NG or SNP haplotype, is an indication that the individual will likely respond to the alpha 7 nicotinic acetylcholine receptor activator treatment.

Furthermore, the disclosure relates to a therapeutic method of increasing the cognitive skills of an individual and/or treatment of individuals suffering from a cognitive impairment, psychotic and/or neurodegenerative disorder comprising the steps of:

III) obtaining the genotype of the individual at the genetic locus of the CYP1A2 gene;

IV) identifying those individuals of step III) CYP1A2 SNP rs2069514-A (SEQ ID NO. 1) or the SNP rs2069514-G (SEQ ID NO. 2) or a SNP forming a haplotype with said SNPs or a SNP in the same linkage disequilibrium with said SNPs, wherein the homozygous presence of the CYP1A2 SNP rs2069514-NA or corresponding SNP haplotype, or heterozygous presence of the CYP1A2 SNP rs2069514-NG or corresponding SNP haplotype is an indication that the individual will likely respond to the alpha 7 nicotinic acetylcholine receptor activator treatment; and V) administering a therapeutic effective amount of an alpha 7 nicotinic acetylcholine receptor activator to those subject identified in step IV).

In an additional embodiment, the above described steps I) and III) further comprising the steps of: VI) obtaining a biological sample of said individual, wherein said sample is selected from the group consisting of blood, blood-derived product (such as buffy coat, serum, and plasma), lymph, urine, tear, saliva, cerebrospinal fluid, buccal swabs, sputum, hair roots, leukocyte sample or tissue samples or any combination thereof, and VII) contacting the biological sample of step VI. with a reagent capable of detecting the (i) CYP1A2 SNP rs2069514-A (SEQ ID NO. 1), or (ii) the CYP1A2 SNP rs2069514-G (SEQ ID NO. 2), or (iii) a SNP forming a haplotype with said SNPs or a SNP in the same linkage disequilibrium with said SNPs.

Preferably, the above mentioned methods are used to treat cognitive impairments, psychotic and/or neurodegenerative disorders in which alpha 7 nicotinic acetylcholine receptor activation plays a role, or is implicated. Hence, in one embodiment, the above mentioned methods further comprising as a first step diagnosing the need for increasing the cognitive skills, or a cognitive impairment, psychotic and/or neurodegenerative disorder in an individual, whereas the cognitive impairments, psychotic and/or neurodegenerative disorders can be selected from the group consisting of mild cognitive impairment, Alzheimer's disease, Parkinson's disease dementia, dementia with Lewy Bodies, schizophrenia, vascular dementia, AIDS-dementia, senile dementia, mild cognitive impairment related to age (MCI), age associated memory impairment, autism, dementias in frontal lobe degenerations, stroke, basal ganglia degenerative disorders, multiple sclerosis, trauma, brain tumors, brain infections, hydrocephalus, depression, toxic or metabolic disorders and drug induced dementias.

In another embodiment of the disclosure the above mentioned methods, the presence of the (i) CYP1A2 SNP rs2069514-A (SEQ ID NO. 1), or (ii) the CYP1A2 SNP rs2069514-G (SEQ ID NO. 2), or (iii) a SNP forming a haplotype with said SNPs or a SNP in the same linkage disequilibrium with said SNPs is determined by using at least one oligonucleotide that specifically hybridizes with specific regions on the nucleic acid molecule carrying said SNP or SNPs. Particularly, the presence of said CYP1A2 SNPs can be detected by sequence-specific primer (SSP) typing, sequence-specific oligonucleotide (SSO) typing, sequence based typing (SBT), DNA amplification such as polymerase chain reaction (PCR), microarray analysis, northern blot analysis, or reverse transcription PCR.

In another aspect of the disclosure, the individuals being selected according to the above describe methods as responders to alpha 7 nicotinic acetylcholine receptor activator treatment for increasing the cognitive skills and/or treatment of a cognitive impairment, psychotic and/or neurodegenerative disorder, are treated with a compound of formula (I). In yet another embodiment, a second cognition enhancer or a therapeutic compound useful for the treatment of cognitive impairments, psychotic and/or neurodegenerative disorders, such as a conventional antipsychotic or an atypical antipsychotic, can be co-administered.

In another embodiment of the disclosed methods the alpha 7 nicotinic acetylcholine receptor activator dose to be administered is from about 2 mg to about 100 mg per day. Another embodiment of the disclosure relates to the use of an alpha 7 nicotinic acetylcholine receptor activator for the treatment of a patient with cognitive impairments, psychotic and/or neurodegenerative disorders or condition in which alpha 7 nicotinic acetylcholine receptor activation plays a role or is implicated, wherein the patient being responsive to the treatment with an alpha 7 nicotinic acetylcholine receptor activator has been selected according to the above described methods.

Furthermore, the disclosure relates to the use of at least one probe for detecting (i) the SNP rs2069514-A (SEQ ID NO. 1), or (ii) the SNP rs2069514-G (SEQ ID NO. 2), or (iii) a SNP forming a haplotype with said SNPs or a SNP in the same linkage disequilibrium with said SNPs for determining whether an individual is responsive to (a) the treatment of cognitive impairments, psychotic and/or neurodegenerative disorders or condition in which alpha 7 nicotinic acetylcholine receptor activation plays a role or is implicated, or (b) the increase of cognitive skills by an alpha 7 nicotinic acetylcholine receptor activator.

In another aspect, the disclosure relates to a kit comprising at least one probe for detecting (i) the SNP rs2069514-A (SEQ ID NO. 1), or (ii) the SNP rs2069514-G (SEQ ID NO. 2), or (iii) a SNP forming a haplotype with said SNPs or a SNP in the same linkage disequilibrium with said SNPs. Preferably, said kit comprises VIII) means for detecting the (i) the SNP rs2069514-A (SEQ ID NO. 1), or (ii) the SNP rs2069514-G (SEQ ID NO. 2), or (iii) a SNP forming a haplotype with said SNPs or a SNP in the same linkage disequilibrium with said SNPs, and IX) instructions how to use said kit.

An additional subject matter of the disclosure relates to the use of a kit, preferably the above disclosed kit, suitable for any of the above described methods or uses, wherein said kit comprises at least one probe for detecting the (i) the SNP rs2069514-A (SEQ ID NO. 1), or (ii) the SNP rs2069514-G (SEQ ID NO. 2), or (iii) a SNP forming a haplotype with said SNPs or a SNP in the same linkage disequilibrium with said SNPs. In a related embodiment, the kit described above comprises oligonucleotide probes.

GENERAL DEFINITIONS

In order that the present invention may be more readily understood, certain terms are first defined. Additional definitions are set forth throughout the detailed description.

The term "comprising" means "including" e.g. a composition "comprising" X may consist exclusively of X or may include something additional e.g. X+Y.

The term "about" in relation to a numerical value x means, for example, x±10%.

The term "cognition enhancer" in the context of this disclosure refers to any drug, supplement, nutraceutical, or functional food that is said to improve mental functions such as cognition, memory, intelligence, motivation, attention, and concentration. Cognition enhancers, as used herein include, but are not limited to cholinergic compounds like acetylcholine esterase inhibitors and/or buturylesterase inhibitors (rivastigmine, donezepil, galantamine, huperzine), ampakines (e.g. CX614, CX516), muscarinic modulators (e.g. muscarinic receptor agonists), modulators of the NMDA-receptor (e.g. positive modulators, antagonists, memantine), phosphodiesterase inhibitors (e.g. PDE4 inhibitors), nootropic compounds like hydergine, oxiracetam, aniracetam, acetyl-L-carnitine, ginkgo-derived compounds, compounds contained in gerovitals like p-aminobenzoic acid and dithylaminoethanol and derivative thereof and attention-modulating compounds like methylphenicate, tomoxetine and modafinil.

The term "conventional antipsychotics" denotes compounds that are effective in treating psychoses mainly via dopamine receptor D2 antagonism. "Conventional antipsychotics" as used herein includes, but is not limited to haloperidol, droperidol, molindone, fluphenazine, thiotixene, flupentixol, promazine, pimozide, chlorpromazine, methotrimeprazine, pipotiazine trifluoperazine, thioridazine, acetophenazine, chlorprothixene and mesoridazine.

The term "atypical antipsychotics" denotes compounds that are effective in treating psychoses via an additional and/or different mechanism than dopamine receptor 2 antagonism. "Atypical antipsychotics" as used herein includes, but is not limited to clozaril, risperidone, olanzapine, quetiapine, ziprasidone, aripiprazol, sertindole, perphenazine, mesoridazine, prochlorperazine, naproxene and loxapine.

As used herein, the term alpha 7 nicotinic acetylcholine receptor activator (α7-nAChR activators) refers to α7-nAChR agonists and α7-nAChR positive allosteric modulators, particularly to low molecular weight (LMW) compounds as disclosed herein.

The term "SNP" in the context of this disclosure refers to a "single nucleotide polymorphism". A "SNP" is a genetic variation between individuals; e.g., a single base position in the DNA of organisms that is variable. A SNP defines a specific allele of a given gene. As used herein, "SNPs" is the plural of SNP. A SNP occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). SNPs are most frequently diallelic. A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference. A SNP may also refer to a polymorphic site on a single chromosome or within a region of a single chromosome, wherein the SNP might refer to an insertion or deletion of several base pairs. Hence, the term "SNP" refers also to a region of a gene having one of several nucleotide sequences found in that region of the gene in different individuals in a population. Although most SNPs are rare, it has been estimated that there are 5.3 million common SNPs, each with a frequency of 10-50%, that account for the bulk of the DNA sequence difference between humans. Such SNPs are present in the human genome once every 600 base pairs (Kruglyak and Nickerson, Nature Genet. 27:235 (2001)). Alleles (variants) making up blocks of such SNPs in close physical proximity are often correlated, resulting in reduced genetic variability and defining a limited number of "SNP haplotypes" (Fullerton, et al., Am. J. Hum. Genet. 67:881 (2000)).

The term "gene" refers to a coding region operably linked to appropriate regulatory sequences capable of regulating the expression of the polypeptide in some manner. A gene includes untranslated regulatory regions of DNA (e.g., promoters, enhancers, repressors, etc.) preceding (upstream) and following (downstream) the coding region (open reading frame, ORF) as well as, where applicable, intervening sequences (i.e., introns) between individual coding regions (i.e., exons). Genes may also include sequences located on both the 5'- and 3'-end of the sequences, which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers, which control or influence the transcription of the gene. The 3'-flanking region may contain sequences, which direct the termination of transcription, posttranscriptional cleavage and polyadenylation.

The term "mild cognitive impairment" (MCI) in the context of this disclosure refers to a cognitive impairment beyond that expected for an individual of a certain age and education, but that do not interfere significantly with the daily activities of such an individual (Petersen R C, Smith G E, Waring S C, Ivnik R J, Tangalos E G, Kokmen E (1999). "Mild cognitive impairment: clinical characterization and outcome". Arch. Neurol. 56 (3): 303-8.)

The term "haplotype" in the context of this disclosure refers to a group of SNPs that do not appear to recombine independently and that can be grouped together in blocks of SNPs. Hence, SNPs that constitute a haplotype are in linkage disequilibrium and thus tend to be inherited together. "Haplotype" also refers to the particular combinations of polymorphic variants (SNPs and/or alleles) observed in a population at polymorphic sites on a single chromosome or within a region of a single chromosome. A "haplotype," as described herein, refers to any combination of SNPs or polymorphic sites. A haplotype can comprise two or more SNPs/alleles and the length of a genome region comprising a haplotype may vary from few hundred bases up to hundreds of kilo bases. It is recognized by those skilled in the art that the same haplotype can be described differently by determining the haplotype defining alleles from different nucleic acid strands. SNPs described herein are differentially present in human individuals and their specific sequence is indicative for the responsiveness to alpha 7 nicotinic acetylcholine receptor activator treatment. Therefore, these SNPs and the haplotypes comprising said SNPs have diagnostic value for risk assessment and treatment efficacy in an individual. Detection of SNPs or polymorphic regions forming haplotypes can be accomplished by methods known in the art used for detecting nucleotides at polymorphic sites (see also definition of Linkage disequilibrium below).

"Linkage disequilibrium" or "LD" refers to a situation, in which two or more allelic variants are linked, i.e., there is a non-random correlation between allelic variants at two or more polymorphic sites in individuals in a population. LD is commonly denoted by a capital D. Normalizing D by dividing it by the theoretical maximum for the observed allele frequencies results in D'. A value of 0 for D' indicates that the examined loci are in fact independent of one another, while a value of 1 demonstrates complete dependency. Two or more allelic variants/SNPs that are linked are said to be in linkage disequilibrium. In general, allelic variants that are part of a haplotype or haplotype block are in linkage disequilibrium. A variety of methods/metrics are known in the art to evaluate the extent to which any two polymorphic variants (alleles) or SNPs are in LD. Suitable metrics include D', r2, and others (see, e.g., Hedrick, P. W., Genetics, 117(2):331-41, 1987). As used herein, polymorphic variants or SNPs are in "strong LD", and forming a haplotype if D'>0.8.

The term "subject" as used herein refers preferably to a human being, especially to a patient being diagnosed with a cognitive impairment, schizophrenia or another mental disease which is a acquired deficit in one or more of memory function, problem solving, orientation and/or abstraction that impinges on an individual's ability to function independently. Subject, patient or individual are used interchangeably.

The term "cognitive disorders/impairments" and "psychotic and/or neurodegenerative disorders" refer to a mental diseases which are acquired deficits in one or more of memory function, problem solving, orientation and/or abstraction that impinges on an individual's ability to function independently. Examples of said disorders are Alzheimer's disease, Lewy Body Dementia, Amyotrophic Lateral Sclerosis, memory impairment, memory loss, cognition deficit, attention deficit, hyperactivity Disorder, schizophrenia, Parkinson's disease, dementia and vascular dementia.

DETAILED DESCRIPTION OF THE INVENTION

It has been discovered that genetic variants present on the human cytochrome P450, family 1, subfamily A, polypeptide 2 (CYP1A2) gene (SEQ ID NO. 3) is a marker for predicting therapeutic responsiveness to an α7-nAChR activator therapy in a subject suffering from cognitive impairments or dysfunctions, psychotic and/or neurodegenerative disorders. CYP1A2 is the major enzyme involved in caffeine metabolism, but its expression is influenced by a number of environmental factors, including smoking. Nicotinic acetylcholine receptors (nAChRs) are members of a superfamily of ligand-gated ion channels that mediate fast signal transmission at synapses. The herein disclosed teaching provides a method for treating cognitive impairments or dysfunctions, psychotic and/or neurodegenerative disorders with α7-nAChR activators, based upon the presence of certain indicative SNPs in the human CYP1A2 gene.

The methods, compositions and kits of the present invention therefore provide a means for selecting patients suffering from cognitive impairments or dysfunctions, psychotic and/or neurodegenerative disorders that are more likely to respond α7-nAChR activator therapy, thereby enhancing the therapeutic efficacy of such treatments.

Therefore, in one aspect, the invention provides a composition comprising an alpha 7 nicotinic acetylcholine receptor activator for the treatment of cognitive impairments, psychotic and/or neurodegenerative disorders in a selected patient population, wherein the patient population is selected on the basis of the genotype of the patients at the human cytochrome P450, family 1, subfamily A, polypeptide 2 (CYP1A2) gene and wherein said genotype is indicative of efficacy of alpha 7 nicotinic acetylcholine receptor activator treatment. The specific marker for predicting therapeutic responsiveness to an α7-nAChR activator therapy can be a SNP and/or a polymorphic region. The skilled person is aware of the nucleic acid sequence and the location of the CYP1A2 gene (located on the human chromosome: 15 (NC_000015.9 (75,041,184 . . . 75,048,941).

In order that the present invention may be more readily understood, the SNPs disclosed herein are defined as follows:

| SNP name and SEQ ID | Sequence |
| --- | --- |
| rs2069514<br>(SEQ ID NO. 1 or 2)<br>rs2069514-A<br>(SEQ ID NO. 1)<br>rs2069514-G<br>(SEQ ID NO. 2) | CGAATTGTAACAAATATATTACACCACTGCAAGATGTTAATAATAGGGGAA<br>ACTGCAGAGTGGGGGTGGTAAATGGCCACTTTTACCTCCCTCATCATACT<br>TTCCACTCAATTTTTCTGTGAACCAAAGACTGCTCTAAAAAAATCTATTAGC<br>TTTTTAAAATTCCTTGGCTCCCCTCCAAAAAGTGTACATATGACATGATCT<br>CATTTATGTAAAATACAACAAGCAAAACAAATCCATGCAATAGATGTTGGG<br>GTCATGGGTACCCTTGAGAAAGGAACACAACGGGACTTCTTGGATGCTTA<br>TGATGTCTCTTGATTAGAGCTGGTTATATGTGTGTTTGTTAAGTTTGCAAA<br>AATTCATCAAGCTACACATGATCGAGCTATACATGACATATGCACTTTTCC<br>ATTTATTTATTTATTTTTGAGACAGAATCTTGCTCTGTCACCCAGGCTGGA<br>GTGCAGTGGTGCGATCTTGGCTCACCGCAACCTCCGCCTCTC [A/G]<br>GATTCAAGCAATTGTCATGCCCCAGCTTCCCGAGTAGCTGGAATTACAGG<br>TGTGCACCATCACGCCCAGCTAATTTTTTTTGTATTTTTAGTAGAGATGA<br>GGTTTCACTATGTTGGCCAGGCTGGTCTTGAACTCCTGGCCTCACTCAAG<br>TGATCCTCCCACCTCGGCCTCCCAAAGTGCTAGAATTACAGGTGTGAGTC<br>ACCGGTCCCAGCTGACATATGCACTTTTCTATATTGTATCCTGTAATTTAA<br>TTTTTTTAAGTTTTAAGAAAACATTAAAAATAAAAAGATAAATAGTCTGTCAT<br>ACAGGAGAATTTCAAATAGTTTATGGAGATAATCCCCCCTCAAGGAGAAG<br>GAGCGTAATCCCCCACTCCTTCGGTGTGGGCTGTGCATAGTGACTTCCTT<br>CCAAAAGGTACAGTATGGAAAGGTGGGAAAGGAGTAACTTTACAGTGAAG<br>AGACCTGACACGCACTACCTTAGCCAGGTGATCAAGGTCAACATC |

Preferably, the mentioned composition is used as described herein to treat cognitive impairments, psychotic and/or neurodegenerative disorders in which alpha 7 nicotinic acetylcholine receptor activation plays a role or is implicated by increasing the cognitive skills of an individual. In one embodiment the cognitive impairments, psychotic and/or neurodegenerative disorders are selected from the group consisting of mild cognitive impairment, Alzheimer's disease, Parkinson's disease dementia, dementia with Lewy Bodies, vascular dementia, AIDS-dementia, senile dementia, mild cognitive impairment related to age (MCI), age associated memory impairment, autism, dementias in frontal lobe degenerations, stroke, basal ganglia degenerative disorders, multiple sclerosis, trauma, brain tumors, brain infections, hydrocephalus, depression, toxic or metabolic disorders and drug induced dementias. In another embodiment of the invention the mentioned composition is used as described herein to treat patients suffering from schizophrenia.

Treatment of the patient population selected based upon the presence of certain indicative SNPs in the human CYP1A2 gene with α7-nAChR activators leads to statistically relevant improved visual learning and memory capabilities, improved cognitive function, improved reasoning and problem solving capabilities and improvements on attention and vigilance compared to individuals not carrying the indicative SNPs, whereas the improvements, measured as effect size as described in the Example section, are at least 0.1, or 0.2, or 0.3, or 0.4 or above 0.5. The effect size values will differ depending on the applied tests and treatment condition.

The phrase "increasing the cognitive skills of an individual" refers to a situation in which (i) the cognitive skills or capabilities, the physiological condition and/or the psychological condition of an individual would be considered by a skilled person as being outside of the normal range of a healthy individual, and (ii) wherein treatment with the compositions of the invention or according to the inventive method leads to a significant improvement compared to individuals of a control group (e.g. individuals who do not carry an indicative marker SNP) or placebo group. The improvement can be complete (e.g. the skilled person would consider the patient as being inside the normal range) or partial, such that the peculiarity of the above mentioned condition in a subject is significantly less pronounced than had the subject not received a composition or treatment according to the present invention. Partial treatment results may lead to a decrease in severity of the above mentioned conditions or disease symptoms, an increase in frequency and duration of disease symptom-free periods, or a prevention of impairment or disability due to the disease affliction. In this context, the term "significantly less pronounced" refers to a conditions or status of a person which, on the basis of measurement of relevant parameter, would after the treatment with the compositions of the invention or according to the inventive method, not be considered by a skilled person as being completely healthy (parameters might be still outside the normal range), but where a significant improvement (which could be an increase or decrease of a certain parameter) of a relevant parameter has been observed. A significant improvement or decrease can be identified for example by comparison of the treatment results of individual patients compared to individuals of a control group (e.g. individuals who do not carry an indicative marker SNP) or placebo group. The skilled person is well aware of the relevant parameter for cognitive skills or capabilities, physiological condition and/or psychological condition of an individual and how to determine them. Said parameters might be selected by a skilled person (e.g. a physician) on the basis of the investigated age-related condition. The phrase "increasing the cognitive skills of an individual" refers also to a situation in which an individual that would be considered (regarding cognitive skills or capabilities) by a skilled person as being inside of the normal range of a healthy individual wants to increase its cognitive skills or capabilities.

In one embodiment, the composition is used in patient populations selected on the basis of carrying the human CYP1A2 SNP rs2069514-A as disclosed in SEQ ID NO. 1. The SNP rs2069514 is a A/G allele (SEQ IDs NO. 1 and 2) with a base pair length of 1 located at position 75,038,220 of the human chromosome 15, on the promoter region of the CYP1A2 gene.

The skilled person is aware of the fact that several SNPs or polymorphic regions exist in the human CYP1A2 gene or in the genomic regions of the human chromosome 15 forming a haplotype with the SNP rs2069514-A (SEQ ID NO. 1) or the SNP rs2069514-G (SEQ ID NO. 2). Said SNPs or polymorphic regions might be located in an area of about 100000, or about 50000, or about 30000, or about 20000, or about 10000 base pairs upstream and downstream of the position of the SNP rs2069514-A (SEQ ID NO. 1) or the SNP rs2069514-G (SEQ ID NO. 2). SNPs or polymorphic regions forming a haplotype with the SNP rs2069514-A (SEQ ID NO. 1) or the SNP rs2069514-G (SEQ ID NO. 2) will be equally suited to be used as markers for predicting therapeutic responsiveness to an α7-nAChR activator. The skilled person is aware of methods to identify other SNPs or polymorphic regions forming a haplotype with the SNP rs2069514-A (SEQ ID NO. 1) or the SNP rs2069514-G (SEQ ID NO. 2) ((see, e.g., Hedrick, P. W., Genetics, 117(2):331-41, 1987 and definition section above). Therefore, in another aspect, the invention provides a composition comprising an alpha 7 nicotinic acetylcholine receptor activator for the treatment of patients suffering from cognitive impairments, psychotic and/or neurodegenerative disorders, aiming to increase the cognitive skills of aid patients, wherein the patient population is selected on the basis of the presence of a SNP or polymorphic region forming a haplotype with the SNP rs2069514-A (SEQ ID NO. 1) or the SNP rs2069514-G (SEQ ID NO. 2).

In another embodiment of the invention, the composition for treatment of patients suffering from cognitive impairments, psychotic and/or neurodegenerative disorders is used in patients selected on the basis of being homozygous/heterozygous for the above mentioned indicative CYP1A2 SNPs or the indicative CYP1A2 SNP haplotypes, particularly wherein the selected patients are homozygous for the indicative CYP1A2 SNP rs2069514-A/A (SEQ ID NO. 1) or corresponding indicative CYP1A2 SNP haplotypes and/or heterozygous for the indicative CYP1A2 SNP rs2069514-A/G or corresponding indicative CYP1A2 SNP haplotypes.

LMW α7-nAChR Activators:
LMW α7-nAChR Agonists:

In one embodiment, the α7-nAChR activator used is an α7-nAChR agonist.

An α7-nAChR agonist is a compound that binds to a receptor comprising an α7-nAChR subunit in vivo and in vitro and is activating the receptor. Activation can be measured by the method disclosed in WO2001/85727, i.e. a functional affinity assay at the homomeric α7-nAChR carried out with a rat pituitary cell line stably expressing the α7-nAChR. As read out, the calcium influx upon stimulation of the receptor compared to epibatidine is used. "α7-nAChR agonists" according to the invention typically induce calcium influx of at least 50% of the maximal influx evoked by epibatidine with an $EC_{50}$ value of at least 1 μM; preferred agonists induce calcium influx of at least 75% of the maximal influx evoked by epibatidine with an $EC_{50}$ value of at least 400 nM; more preferred agonists induce calcium influx of at least 85% of the maximal influx evoked by epibatidine with an $EC_{50}$ value of at least 50 nM.

Preferred α7-nAChR agonists should be well absorbed from the gastrointestinal tract, should be sufficiently metabolically stable and possess favorable pharmacokinetic properties. Further preferred α7-nAChR agonists bind in-vivo potently to α7-nAChRs whilst showing little affinity for other receptors, especially for other nAChRs, e.g. α4β2 nAChR, for muscarinic acetylcholine receptors, e.g. M1, and/or the 5-$HT_3$ receptor. Further preferred α7-nAChR agonists cross the blood brain barrier effectively. Preferred α7-nAChR agonists should be non-toxic and demonstrate few side-effects. Furthermore, a preferred α7-nAChR agonist will be able to exist in a physical form that is stable, non-hygroscopic and easily formulated.

In one embodiment, the α7-nAChR agonist is a selective α7-nAChR agonist, i.e. is selective for a receptor comprising an α7-nAChR subunit, since such an agonist would be expected to cause fewer side effects than a non-selective agonist to a treated subject. An agonist being selective for a receptor comprising an α7-nAChR subunit has a functional affinity to such a receptor to a much higher degree, e.g. at least 10-fold affinity difference in $EC_{50}$ value, preferably at least 20-fold, more preferably at least 50-fold, compared to any other nicotinic acetylcholine receptor. To assess the affinity of the α7-nAChR agonists of the invention on other nicotinic acetylcholine receptors, the method disclosed in WO2001/85727 can be used, i.e. to assess the affinity on human α4β2 nAChR, a similar functional assay is carried out using a human embryonic kidney cell line stable expressing the human α4β2 subtype and to assess the activity of the compounds of the invention on the "ganglionic subtype" and the "muscle type" of nicotinic receptor, similar functional assays are carried out with a human embryonic kidney cell line stably expressing the human "ganglionic subtype" or a cell line endogenously expressing the human "muscle type" of nicotinic receptors.

In the last 15 years much effort has been focused on developing selective α7 nAChR agonists leading to the discovery of many different chemotypes displaying said selective activity. These efforts are summarized the review from Horenstein et al (Mol Pharmacol, 2008, 74, 1496-1511, which describes no less than 9 different families of α7 nAChR agonists, in most of which selective agonists have been found. In fact, several drug candidates having an α7 nAChR agonist mode of action entered pre-clinical or even clinical testing (for review: Broad et al, Drugs of the Future, 2007, 32(2), 161-170; Romanelli et al, Expert Opin Ther Patents, 2007, 17(11), 1365-1377). Examples of such compounds—again belonging to a diversity of chemotypes—are MEM3454, MEM63908, SSR180711, GTS21, EVP6124, ABT107, ABT126, TC-5619, AZD-6319 and SAR-130479. Further α7 nAChR agonists and their use as pharmaceuticals are known, for example, from WO2001/85727, WO2004/022556, WO2005/123732, WO2006/005608, WO2007/045478, WO2007/068476 and WO2007/068475.

In one embodiment, the α7-nAChR agonist has a maximum molecular weight of 1500 dalton. In one embodiment, the α7-nAChR agonist has a maximum molecular weight of 1000 dalton. In one embodiment, the α7-nAChR agonist has a maximum molecular weight of 800 dalton. In one embodiment, the α7-nAChR agonist has a maximum molecular weight of 500 dalton.

In one embodiment, the α7-nAChR agonist is a compound of formula (I)

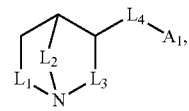

wherein
$L_1$ is —$CH_2$—; $L_2$ is —$CH_2$— or —$CH_2$—$CH_2$—; and $L_3$ is —$CH_2$— or —$CH(CH_3)$—; or
$L_1$ is —$CH_2$—$CH_2$—; $L_2$ is —$CH_2$—; and $L_3$ is —$CH_2$—$CH_2$—;
$L_4$ is a group selected from

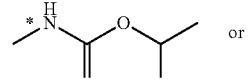

L4a

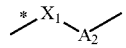

L4b wherein the bond marked with the asterisk is attached to the azabicycloalkyl moiety;
$R_1$ is hydrogen or $C_{1-4}$alkyl;
$X_1$ is —O— or —NH—;
$A_2$ is selected from

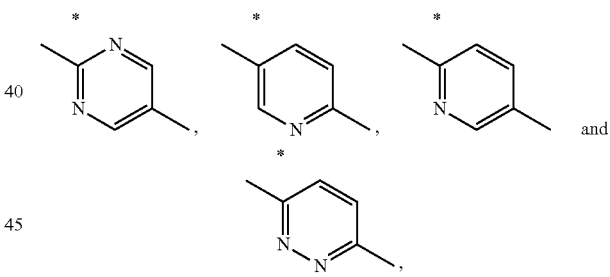

wherein the bond marked with the asterisk is attached to $X_1$;
$A_1$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_2$, and wherein a substituent on a nitrogen in a heterocyclic ring system may not be halogen;
each $R_2$ independently is $C_{1-6}$alkyl, $C_{1-6}$halogenalkyl, $C_{1-6}$alkoxy, $C_{1-6}$halogenalkoxy, halogen, cyano or a three- to six-membered monocyclic ring system which may be aromatic, saturated or partially saturated and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;

or two $R_2$ at adjacent ring atoms form a $C_{3-4}$alkylene group, wherein 1-2 carbon atoms may be replaced by $X_2$, and wherein the $C_{3-4}$alkylene group may be substituted once or more than once by $R_3$;

each $X_2$ independently is —O— or —N($R_4$)—;
each $R_4$ independently is hydrogen or $C_{1-6}$alkyl; and
each $R_3$ independently is halogen or $C_{1-6}$alkyl;
in free base form or in acid addition salt form.

Unless indicated otherwise, the expressions used in this invention have the following meaning:

"Alkyl" represents a straight-chain or branched-chain alkyl group, for example, methyl, ethyl, n- or iso-propyl, n-, iso-, sec- or tert-butyl, n-pentyl, n-hexyl; $C_{1-6}$alkyl preferably represents a straight-chain or branched-chain $C_{1-4}$alkyl with particular preference given to methyl, ethyl, n-propyl, iso-propyl and tert-butyl.

Each alkyl part of "alkoxy", "halogenalkyl" and so on shall have the same meaning as described in the abovementioned definition of "alkyl", especially regarding linearity and preferential size.

A substituent being substituted "once or more than once", for example as defined for $A_1$, is preferably substituted by one to three substituents.

Halogen is generally fluorine, chlorine, bromine or iodine; preferably fluorine, chlorine or bromine. Halogenalkyl groups preferably have a chain length of 1 to 4 carbon atoms and are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,2-trichloroethyl, 1,1,2,2-tetrafluoroethyl, 2,2,3,3-tetrafluoropropyl, 2,2,3,3,3-pentafluoropropyl or 2,2,3,4,4,4-hexafluorobutyl; preferably —CF3, —CHF2, —CH2F, —CHF—CH3, —CF2CH3, or —CH2CF3.

In the context of the invention, the definitions of "two R2 at adjacent ring atoms form a C3-4alkylene group, wherein 1-2 carbon atoms may be replaced by X2" or "two R5 at adjacent ring atoms form a C3-4alkylene group, wherein 1-2 carbon atoms may be replaced by X3" encompass —CH2—CH2—CH2—, —CH2—CH2—CH2—CH2—, —O—CH2—O—, —O—CH2—CH2—O— and —CH2—CH2—NH—. An example of a substituted group is —CH2—CH2—N(CH3)—.

In the context of the invention, the definition of $A_1$ or $A_3$ as a "five- to ten-membered monocyclic or fused polycyclic aromatic ring system" encompasses a $C_6$- or $C_{10}$-aromatic hydrocarbon group or a five- to ten-membered heterocyclic aromatic ring system. "Polycyclic" means preferably bicyclic.

In the context of the invention, the definition of $R_2$ as a "three- to six-membered monocyclic ring system" encompasses a $C_6$-aromatic hydrocarbon group, a five- to six-membered heterocyclic aromatic ring system and a three- to six-membered monocyclic aliphatic or heterocyclic ring system.

A $C_6$- or $C_{10}$-aromatic hydrocarbon group is typically phenyl or naphthyl, especially phenyl.

Preferably, but also depending on substituent definition, "five- to ten-membered heterocyclic aromatic ring systems" consist of 5 to 10 ring atoms of which 1-3 ring atoms are hetero atoms. Such heterocyclic aromatic ring systems may be present as a single ring system or as bicyclic or tricyclic ring systems; preferably as single ring systems or as benzannelated ring systems. Bicyclic or tricyclic ring systems may be formed by annelation of two or more rings, or by a bridging atom, e.g. oxygen, sulfur, nitrogen. Examples of heterocyclic ring systems are: imidazo[2,1-b]thiazole, pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, isothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pteridine, and the corresponding benz-annelated heterocycles, e.g. indole, isoindole, coumarin, isoquinoline, quinoline and the like. Preferred heterocycles are: imidazo[2,1-b]thiazole, oxazole, isoxazole, thiazole, isothiazole, triazole, pyrrole, furane, tetrahydrofurane, pyridine, pyrimidine, imidazole or pyrazole.

In the context of the invention, three- to six-membered monocyclic aliphatic ring systems are typically cyclopropyl, cyclobutyl, cyclopentyl or cyclohexyl.

On account of asymmetrical carbon atom(s) that may be present in the compounds of formula (I) and compounds of formula (II), the compounds may exist in optically active form or in form of mixtures of optical isomers, e.g. in form of racemic mixtures or diastereomeric mixtures. All optical isomers and their mixtures, including racemic mixtures, are part of the present invention.

In one embodiment, the α7-nAChR agonist is a compound of formula (I)

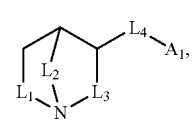

(I)

wherein
$L_1$ is —CH2—; $L_2$ is —CH2—CH2—; and $L_3$ is —CH2— or —CH(CH3)—;
$L_4$ is a group selected from

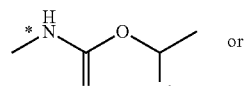

L4a

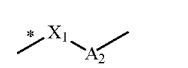

L4b wherein the bond marked with the asterisk is attached to the azabicycloalkyl moiety;
$R_1$ is hydrogen or $C_{1-4}$alkyl;
$X_1$ is —O— or —NH—;
$A_2$ is selected from

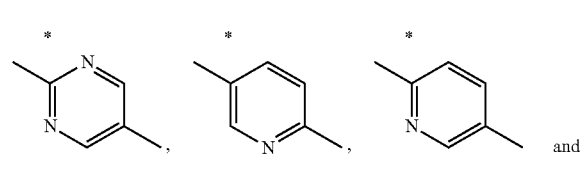

and

-continued

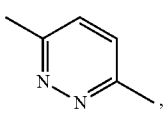

wherein the bond marked with the asterisk is attached to $X_1$;

$A_1$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_2$, and wherein a substituent on a nitrogen in a heterocyclic ring system may not be halogen; and each $R_2$ independently is $C_{1-6}$alkyl, $C_{1-6}$halogenalkyl, $C_{1-6}$alkoxy, $C_{1-6}$halogenalkoxy or halogen.

In one embodiment, the α7-nAChR agonist is a compound of formula (I)

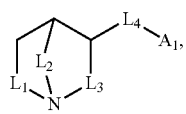

(I)

wherein $L_1$ is —$CH_2$—; $L_2$ is —$CH_2$—$CH_2$—; and $L_3$ is —$CH_2$—;

$L_4$ is

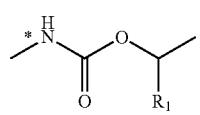

L4a wherein the bond marked with the asterisk is attached to the azabicycloalkyl moiety;

$R_1$ is hydrogen or $C_{1-4}$alkyl;

$A_1$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_2$, and wherein a substituent on a nitrogen in a heterocyclic ring system may not be halogen; and each $R_2$ independently is $C_{1-6}$alkyl, $C_{1-6}$halogenalkyl, $C_{1-6}$alkoxy, $C_{1-6}$halogenalkoxy or halogen.

In one embodiment, the α7-nAChR agonist is a compound of formula (I)

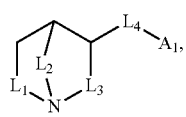

(I)

wherein $L_1$ is —$CH_2$—; $L_2$ is —$CH_2$—$CH_2$—; and $L_3$ is —$CH_2$— or —$CH(CH_3)$—;

$L_4$ is

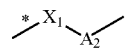

L4b wherein the bond marked with the asterisk is attached to the azabicycloalkyl moiety;

$X_1$ is —O— or —NH—;

$A_2$ is selected from

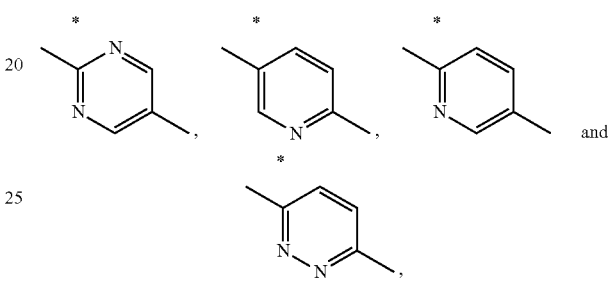

and wherein the bond marked with the asterisk is attached to $X_1$;

A is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_2$, and wherein a substituent on a nitrogen in a heterocyclic ring system may not be halogen; and each $R_2$ independently is $C_{1-6}$alkyl, $C_{1-6}$halogenalkyl, $C_{1-6}$alkoxy, $C_{1-6}$halogenalkoxy or halogen.

In one embodiment, the α7-nAChR agonist is a compound of formula (I)

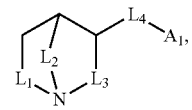

(I)

wherein $L_1$ is —$CH_2$—$CH_2$—; $L_2$ is —$CH_2$—; and $L_3$ is —$CH_2$—$CH_2$—;

$L_4$ is

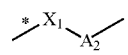

L4b wherein the bond marked with the asterisk is attached to the azabicycloalkyl moiety;

$X_1$ is —O— or —NH—;

A₂ is selected from

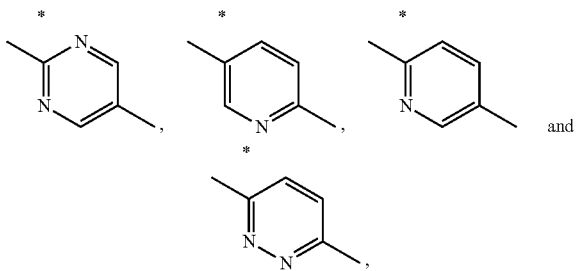

wherein the bond marked with the asterisk is attached to X₁;

A₁ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by R₂, and wherein a substituent on a nitrogen in a heterocyclic ring system may not be halogen; and each R₂ independently is $C_{1-6}$alkyl, $C_{1-6}$halogenalkyl, $C_{1-6}$alkoxy, $C_{1-6}$halogenalkoxy or halogen.

In one embodiment, the α7-nAChR agonist is a compound selected from Group P1;

Group P1 is the group consisting of

A-1: (S)-(1-aza-bicyclo[2.2.2]oct-3-yl)-carbamic acid (S)-1-(2-fluoro-phenyl)-ethyl ester;
A-2: (R)-(1-aza-bicyclo[2.2.2]oct-3-yl)-carbamic acid (R)-1-(2-chloro-phenyl)-ethyl ester;
A-3: (S)-(1-aza-bicyclo[2.2.2]oct-3-yl)-carbamic acid (S)-1-phenyl-ethyl ester;
B-1: (R)-3-(5-phenyl-pyrimidin-2-yloxy)-1-aza-bicyclo[2.2.2]octane;
B-2: (R)-3-(5-p-tolyl-pyrimidin-2-yloxy)-1-aza-bicyclo[2.2.2]octane;
B-3: (R)-3-(5-(2-fluoro-4-methyl-phenyl)-pyrimidin-2-yloxy)-1-aza-bicyclo[2.2.2]octane;
B-4: (R)-3-(5-(3,4-dimethyl-phenyl)-pyrimidin-2-yloxy)-1-aza-bicyclo[2.2.2]octane;
B-5: (R)-3-(6-p-tolyl-pyridin-3-yloxy)-1-aza-bicyclo[2.2.2]octane;
B-6: (R)-3-(6-phenyl-pyridin-3-yloxy)-1-aza-bicyclo[2.2.2]octane;
B-7: (R)-3-(6-(3,4-dimethyl-phenyl)-pyridin-3-yloxy)-1-aza-bicyclo[2.2.2]octane;
B-8: (R)-3-[6-(2-fluoro-4-methyl-phenyl)-pyridazin-3-yloxy]-1-aza-bicyclo[2.2.2]octane;
B-9: (R)-3-[6-(4,5-dimethyl-2-fluoro-phenyl)-pyridazin-3-yloxy]-1-aza-bicyclo[2.2.2]octane;
B-10: (R)-3-[6-(3,4-dimethyl-phenyl)-pyridazin-3-yloxy]-1-aza-bicyclo[2.2.2]octane;
B-11: (R)-3-[6-(4-methyl-phenyl)-pyridazin-3-yloxy]-1-aza-bicyclo[2.2.2]octane;
B-12: (R)-3-[6-(2,5-difluoro-4-methyl-phenyl)-pyridazin-3-yloxy]-1-aza-bicyclo[2.2.2]octane;
B-13: (2S,3R)-3-[6-(1H-indol-5-yl)-pyridazin-3-yloxy]-2-methyl-1-aza-bicyclo[2.2.2]octane;
B-14: (2R,3S)-3-[6-(1H-indol-5-yl)-pyridazin-3-yloxy]-2-methyl-1-aza-bicyclo[2.2.2]octane;
B-15: (2S,3R)-3-[5-(1H-indol-5-yl)-pyrimidin-2-yloxy]-2-methyl-1-aza-bicyclo[2.2.2]octane;
B-16: (2R,3S)-3-[5-(1H-indol-5-yl)-pyrimidin-2-yloxy]-2-methyl-1-aza-bicyclo[2.2.2]octane;
B-17: 3-[6-(1H-indol-5-yl)-pyridin-3-yloxy]-2-methyl-1-aza-bicyclo[2.2.2]octane;
B-18: (2S,3R)-2-methyl-3-[6-(5-methyl-thiophen-2-yl)-pyridazin-3-yloxy]-1-aza-bicyclo[2.2.2]octane;
B-19: 3-[6-(2,3-dimethyl-1H-indol-5-yl)-pyridazin-3-yloxy]-2-methyl-1-aza-bicyclo[2.2.2]octane;
B-20: trans-2-methyl-1-aza-bicyclo[2.2.2]oct-3-yl)-(6-phenyl-pyridin-3-yl)-amine;
B-21: trans-[6-(1H-indol-5-yl)-pyridin-3-yl]-(2-methyl-1-aza-bicyclo[2.2.2]oct-3-yl)-amine;
C-1: (4S,5R)-4-[5-(1H-indol-5-yl)-pyrimidin-2-yloxy]-1-aza-bicyclo[3.3.1]nonane;
C-2: 5-{2-[(4S,5R)-(1-aza-bicyclo[3.3.1]non-4-yl)oxy]-pyrimidin-5-yl}-1,3-dihydro-indol-2-one;
C-3: (4S,5R)-4-[6-(1H-indol-5-yl)-pyridin-3-yloxy]-1-aza-bicyclo[3.3.1]nonane;
C-4: (4S,5R)-4-[5-(1H-indol-5-yl)-pyridin-2-yloxy]-1-aza-bicyclo[3.3.1]nonane;
C-5: (4S,5R)-4-[6-(1H-indol-5-yl)-pyridazin-3-yloxy]-1-aza-bicyclo[3.3.1]nonane;
C-6: 5-{6-[(4S,5R)-(1-aza-bicyclo[3.3.1]non-4-yl)oxy]-pyridazin-3-yl}-1,3-dihydro-indol-2-one;
C-7: (1-aza-bicyclo[3.3.1]non-4-yl)-[5-(1H-indol-5-yl)-pyridin-2-yl]-amine;
C-8: (1-aza-bicyclo[3.3.1]non-4-yl)-[5-(1H-indol-5-yl)-pyrimidin-2-yl]-amine;
C-9: (1-aza-bicyclo[3.3.1]non-4-yl)-[6-(1H-indol-5-yl)-pyridin-3-yl]-amine;
C-10: (1-aza-bicyclo[3.3.1]non-4-yl)-[6-(1H-indol-5-yl)-pyridin-3-yl]-amine;
C-11: (1-aza-bicyclo[3.3.1]non-4-yl)-[5-(1H-indol-4-yl)-pyrimidin-2-yl]-amine;
C-12: (1-aza-bicyclo[3.3.1]non-4-yl)-[6-(1H-indol-5-yl)-pyridazin-3-yl]-amine;
D-1: 4-(5-phenyl-1,3,4-thiadiazol-2-yloxy)-1 azatricyclo[3.3.1.1³,⁷]decane having the formula

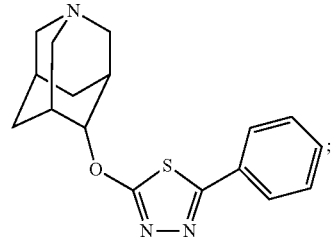 [SMILES: c1ccc(-c2nnc(OC3C4CC5CC3CN(C5)C4)s2)cc1]

D-1a: (4S)-4-(5-phenyl-1,3,4-thiadiazol-2-yloxy)-1 azatricyclo[3.3.1.1³,⁷]decane;
D-1 b: 4-(6-(1H-indol-5-yl)-pyridazin-3-yloxy)-1 azatricyclo[3.3.1.1³,⁷]decane;
D-1c: 4-(6-(1H-indol-5-yl)-pyridin-3-yloxy)-1 azatricyclo[3.3.1.1³,⁷]decane;
D-1 d: 4-(5-(1H-indol-5-yl)-pyrimidin-2-yloxy)-1 azatricyclo[3.3.1.1³,⁷]decane;
D-2: 2-(6-phenylpyridazine-3-yl)octahydropyrrolo[3,4-c]pyrrole having the formula

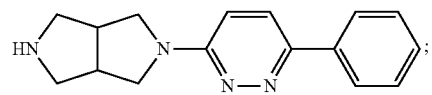 [SMILES: c1ccc(-c2ccc(N3CC4CNCC4C3)nn2)cc1]

D-3: 5-[6-(5-methyl-hexahydro-pyrrolo[3,4-c]pyrrol-2-yl-pyridazin-3-yl1H-indole having the formula

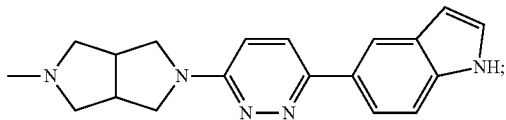

D-3a: 5-[6-(cis-5-methyl-hexahydro-pyrrolo[3,4-c]pyrrol-2-yl-pyridazin-3-yl1H-indole;
D-4: 5-[5-{6-methyl-3,6-diaza-bicyclo[3.2.0]hept-3-yl}-pyridin-2-yl]-1H-indole having the formula

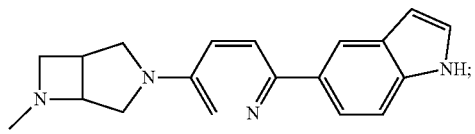 [SMILES: C=C(/C=C\C(=N)c1ccc2[nH]ccc2c1)N1CC2CN(C)C2C1]

D-4a: 5-[5-{(1R,5R)-6-methyl-3,6-diaza-bicyclo[3.2.0]hept-3-yl}-pyridin-2-yl]-1H-indole
D-5: 2-Methyl-5-(6-phenyl-pyridazin-3-yl)-octahydro-pyrrolo[3,4-c]pyrrole having the formula

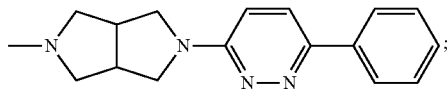 [SMILES: CN1CC2CN(c3ccc(-c4ccccc4)nn3)CC2C1]

D-6: 5-{6-[1-azabicyclo[2.2.2]oct-3-yloxy]pyridazin-3-yl}-1H-indole;
D-6a: 5-{6-[(3R)-1-azabicyclo[2.2.2]oct-3-yloxy]pyridazin-3-yl}-1H-indole;
D-7: 5-{6-[1-azabicyclo[2.2.2]oct-3-yloxy]pyridazin-3-yl}-1,3-dihydro-indol-2-one;
D-7a: 5-{6-[(3R)1-azabicyclo[2.2.2]oct-3-yloxy]pyridazin-3-yl}-1,3-dihydro-indol-2-one;
D-8: N-(1-azabicyclo[2.2.2]oct-3-yl)-1H-indazole-3-carboxamide;
D-8a: N-((3R)-1-azabicyclo[2.2.2]oct-3-yl)-1H-indazole-3-carboxamide
D-8b: N-((3S)-1-azabicyclo[2.2.2]oct-3-yl)-1H-indazole-3-carboxamide
D-9: N-(1-azabicyclo[2.2.2]oct-3-yl)-5-(trifluoromethoxy)-1H-indazole-3-carboxamide;
D-9a: N-((3R)-1-azabicyclo[2.2.2]oct-3-yl)-5-(trifluoromethoxy)-1H-indazole-3-carboxamide;
D-9b: N-((3S)-1-azabicyclo[2.2.2]oct-3-yl)-5-(trifluoromethoxy)-1H-indazole-3-carboxamide;
D-10: N-(2-((3-pyridinyl)methyl)-1-azabicyclo[2.2.2]oct-3-yl)benzofuran-2-carboxamide;
D-10a: (2S,3R)—N-(2-((3-pyridinyl)methyl)-1-azabicyclo[2.2.2]oct-3-yl)benzofuran-2-carboxamide;
D-11: N-(2-((3-pyridinyl)methyl)-1-azabicyclo[2.2.2]oct-3-yl)-3,5-difluorobenzamide;
D-11a: (2S,3R)—N-(2-((3-pyridinyl)methyl)-1-azabicyclo[2.2.2]oct-3-yl)-3,5-difluorobenzamide;
D-11 b: N-(2-((3-pyridinyl)methyl)-1-azabicyclo[2.2.2]oct-3-yl)-5-methylthiophene-2-carboxamide;
D-11c: (2S,3R)—N-(2-((3-pyridinyl)methyl)-1-azabicyclo[2.2.2]oct-3-yl)-5-methylthiophene-2-carboxamide;
D-11d: N-(2-((3-pyridinyl)methyl)-1-azabicyclo[2.2.2]oct-3-yl)-5-(2-pyridinyl)thiophene-2-carboxamide;
D-11e: (2S,3R)—N-(2-((3-pyridinyl)methyl)-1-azabicyclo[2.2.2]oct-3-yl)-5-(2-pyridinyl)thiophene-2-carboxamide;
D-12: 4-(5-methyloxazolo[4,5-b]pyridin-2-yl)-1,4-diazabicyclo[3.2.2]nonane;
D-13: [N-[(3R)-1-azabicyclo[2.2.2]oct-3-yl]-4-chlorobenzamide;
D-14: furo[2,3-c]pyridine-5-carboxylic acid (1-aza-bicyclo[2.2.2]oct-3-yl)-amide;
D-15: 2,3-dihydro-benzo[1,4]dioxine-6-carboxylic acid (1-aza-bicyclo[2.2.2]oct-3-yl)-amide;
D-16: 5-morpholin-4-yl-pentanoic acid (4-pyridin-3-yl-phenyl)-amide;
D-17: N-{4-[4-(2,4-dimethoxy-phenyl)-piperazin-1-yl]-butyl}-4-pyridin-2-yl-benzamide;
D-18: 1-[6-(4-fluorophenyl)pyridin-3-yl]-3-(4-piperidin-1-ylbutyl)-urea;
D-19: 7,8,9,10-tetrahydro-6,10-methano-6H-pyrazino-(2,3-h)(3)-benzazepine;
D-20: (2'R)-spiro-[1-azabicyclo[2.2.2]octane-3,2'(3'H)-furo[2,3-b]pyridine];
D-21: 1,4-Diaza-bicyclo[3.2.2]nonane-4-carboxylic acid 4-bromo-phenyl ester;
D-22: 3-[1-(2,4-Dimethoxy-phenyl)-meth-(E)-ylidene]-3,4,5,6-tetrahydro-[2,3']bipyridinyl;
D-23: 7-(2-Methoxy-phenyl)-benzofuran-2-carboxylic acid (1-aza-bicyclo[2.2.2]oct-3-yl)-amide;
D-24: N-methyl-1-{5-[3'H-spiro[4-azabicyclo[2.2.2]octane-2,2'-furo[2,3-b]pyridin]-5'-yl]-2-thienyl}methanamine having the formula

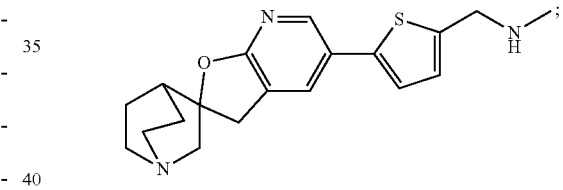

D-24a: N-methyl-1-{5-[(2R)-3'H-spiro[4-azabicyclo[2.2.2]octane-2,2'-furo[2,3-b]pyridin]-5'-yl]-2-thienyl}methanamine;
D-24b: N-methyl-1-{5-[(2S)-3'H-spiro[4-azabicyclo[2.2.2]octane-2,2'-furo[2,3-b]pyridin]-5'-yl]-2-thienyl}methanamine;
D-25a: 6-[(Anilinocarbonyl)amino]-N-[(3R)-1-azabicyclo[2.2.2]oct-3-yl]-1-benzothiophene-2-carboxamide;
D-25b: N-[(3R)-1-Azabicyclo[2.2.2]oct-3-yl]-6-({[(4-chlorophenyl)amino]carbonyl}amino)-1-benzothiophene-2-carboxamide;
D-25c: N-[(3R)-1-Azabicyclo[2.2.2]oct-3-yl]-6-({[(2-methoxyphenyl)amino]carbonyl}-amino)-1-benzothiophene-2-carboxamide;
D-25d: N-[(3R)-1-Azabicyclo[2.2.2]oct-3-yl]-6-({[(4-methoxyphenyl)amino]carbonyl}-amino)-1-benzothiophene-2-carboxamide;
D-25e: N-[(3R)-1-Azabicyclo[2.2.2]oct-3-yl]-6-({[(2-phenylethyl)amino]carbonyl}amino)-1-benzothiophene-2-carboxamide;
D-25f: N-[(3R)-1-Azabicyclo[2.2.2]oct-3-yl]-6-({[(3-cyanophenyl)amino]carbonyl}amino)-1-benziophene-2-carboxamide;
D-25g: N-[(3R)-1-Azabicyclo[2.2.2]oct-3-yl]-6-({[(3-bromophenyl)amino]carbonyl}amino)-1-benzothiophene-2-carboxamide;

D-25h: N-[(3R)-1-Azabicyclo[2.2.2]oct-3-yl]-6-({[(2-ethoxyphenyl)amino]carbonyl)amino)-1-benzothiophene-2-carboxamide;

D-25i: N-[(3R)-1-Azabicyclo[2.2.2]oct-3-yl]-6-({[(4-(dimethylamino)phenyl)amino]-carbonyl)amino)-1-benzothiophene-2-carboxamide;

D-25j: N-(3R)-1-Azabicyclo[2.2.2]oct-3-yl]-6-({[(2-nitrophenyl)amino]carbonyl}amino)-1-benzothiophene-2-carboxamide;

D-25k: N-[(3R)-1-Azabicyclo[2.2.2]oct-3-yl]-6-({[(2,6-difluorophenyl)amino]carbonyl}-amino)-1-benzothiophene-2-carboxamide;

D-25l: N-[(3R)-1-Azabicyclo[2.2.2]oct-3-yl]-6-({[(2,4-dichlorophenyl)amino]carbonyl}-amino)-1-benzothiophene-2-carboxamide;

D-25m: N-[(3R)-1-Azabicyclo[2.2.2]oct-3-yl]-6-[({[3-(trifluoromethyl)phenyl]amino]-carbonyl)amino]-1-benzothiophene-2-carboxamide;

D-25n: N-[(3R)-1-Azabicyclo[2.2.2]oct-3-yl]-6-({[(3,4,5-trimethoxyphenyl)amino]-carbonyl}amino)-1-benzothiophene-2-carboxamide;

D-25o: N-[(3R)-1-Azabicyclo[2.2.2]oct-3-yl]-6-[({[4-methoxy-3-(trifluoromethyl)phenyl]-amino}carbonyl)amino]-1-benzothiophene-2-carboxamide;

D-25p: N-{(3R)-1-Azabicyclo[2.2.2]oct-3-yl]-6-[({[3-methoxyphenyl]amino}carbonyl)-amino]-1-benzothiophene-2-carboxamide;

D-25q: N-[(3R)-1-Azabicyclo[2.2.2]oct-3-yl]-6-[({[3-trifluoromethoxyphenyl]amino}-carbonyl)-amino]-1-benzothiophene-2-carboxamide;

D-25r: N-[(3R)-1-Azabicyclo[2.2.2]oct-3-yl]-6-{[(tert-butylamino)carbonyl]amino}-1-benzothiophene-2-carboxamide;

D-25s: N-[(3R)-1-Azabicyclo[2.2.2]oct-3-yl]-6-{[(cyclohexylamino)carbonyl]amino}-1-benzothiophene-2-carboxamide;

D-25t: N-[(3R)-1-Azabicyclo[2.2.2]oct-3-yl]-6-[({[(1S)-1-phenylethyl]amino}carbonyl-amino]-1-benzothiophene-2-carboxamide;

D-25u: 7-[(Anilinocarbonyl)amino]-N-[(3R)-1-azabicyclo[2.2.2]oct-3-yl]-1-benzothiophene-2-carboxamide;

D-25v: N-[(3R)-1-Azabicyclo[2.2.2]oct-3-yl]-6-({[(4-methoxyphenyl)amino]carbonyl}-amino)-1-benzofuran-2-carboxamide;

D-26a: N-[4-(2-Thienyl)phenyl]-1-azabicyclo[2.2.2]octane-3-carboxamide;

D-26b: N-[4'-(Hydroxymethyl)-1,1'-biphenyl-4-yl]-1-azabicyclo[2.2.2]octane-3-carboxamide;

D-26c: N-(4'-Fluoro-1,1'-biphenyl-4-yl)-1-azabicyclo[2.2.2]octane-3-carboxamide;

D-26d: N-(4'-Methylsulfanyl-1,1'-biphenyl-4-yl)-1-azabicyclo[2.2.2]octane-3-carboxamide;

D-26e: 2-(1-Azabicyclo[2.2.2]oct-3-yl)-N-(4'-fluoro-1,1'-biphenyl-4-yl)acetamide;

D-26f: 2-(1-Azabicyclo[2.2.2]oct-3-yl)-N-(4'-methoxy-1,1'-biphenyl-4-yl)acetamide;

D-26g: 2-(1-Azabicyclo[2.2.2]oct-3-yl)-N-(4'-fluoro-1,1'-biphenyl-3-yl)acetamide;

D-26h: 2-(1-Azabicyclo[2.2.2]oct-3-yl)-N-(3'-nitro-1,1'-biphenyl-4-yl)acetamide;

D-26i: 2-(1-Azabicyclo[2.2.2]oct-3-yl)-N-[4'-(hydroxymethyl)-1-biphenyl-3-yl]acetamide;

D-26j: 2-(1-Azabicyclo[2.2.2]oct-3-yl)-N-[4'-(bromomethyl)-1-biphenyl-4-yl]acetamide;

D-26k: 2-(1-Azabicyclo[2.2.2]oct-3-yl)-N-[2'-(hydroxymethyl)-1,1'-biphenyl-3-yl]acetamide;

D-26l: N-[3'(Acetylamino)-1,1'-biphenyl-4-yl]-2-(1-azabicyclo[2.2.2]oct-3-yl)acetamide;

D-26m: (3R)—N-[2'-(Hydroxymethyl)-1,1'-biphenyl-4-yl]-1-azabicyclo[2.2.2]octane-3-carboxamide;

D-26n: (3R)—N-[4'-(Hydroxymethyl)-1,1'-biphenyl-4-yl]-1-azabicyclo[2.2.2]octane-3-carboxamide;

D-26o: (3S)—N-[4'(Hydroxymethyl)-1,1'-biphenyl-4-yl]-1-azabicyclo[2.2.2]octane-3-carboxamide;

D-26p: (3R)—N-[4'-(4-Morpholinyl)-1,1'-biphenyl-4-yl]-1-azabicyclo[2.2.2]octane-3-carboxamide;

D-26q: (3R)—N-[4'-(Hydroxymethyl)-3'-(methoxy)-1,1'-biphenyl-4-yl]-1-azabicyclo[2.2.2]-octane-3-carboxamide;

D-26r: Methyl 4'-{[(3S)-1-azabicyclo[2.2.2]oct-3-ylcarbonyl]amino}-1,1'-biphenyl-4-carboxylate;

D-26s: 4'-{[(3S)-1-Azabicyclo[2.2.2]oct-3-ylcarbonyl]amino}-1,1'-biphenyl-4-carboxylic Acid;

D-26t: (3R)—N-[4'-(Hydroxy-1-methylethyl)-1,1'-biphenyl-4-yl]-1-azabicyclo[2.2.2]-octane-3-carboxamide;

D-26u: (3R)—N-[4'-(Aminocarbonyl)-1,1'-biphenyl-4-yl]-1-azabicyclo[2.2.2]octane-3-carboxamide;

D-26v: (3R)—N-[4'-(Hydroxymethyl)-3-fluoro-1,1'-biphenyl-4-yl]-1-azabicyclo[2.2.2]octane-3-carboxamide;

D-26w: (4'-{[(3R)-1-Azabicyclo[2.2.2]oct-3-ylcarbonyl]amino}-1,1'-biphenyl-4-yl)methyl Methylcarbamate;

D-26x: (4'-{[(3R)-1-Azabicyclo[2.2.2]oct-3-ylcarbonyl]amino}-1,1'-biphenyl-4-yl)methyl Isopropylcarbamate;

D-26y: (4'-{[(3R)-1-Azabicyclo[2.2.2]oct-3-ylcarbonyl]amino}-1,1'-biphenyl-4-yl)methyl Ethylcarbamate;

D-26z: the free base form of a compound being selected from Examples No 26, 27, 28, 29, 30, 31, 32, 33, 34 and 35 of WO2003/078431;

D-27a: 2-(1-Azabicyclo[2.2.2]oct-3-yl)-N-(7-bromo-1-benzothien-2-yl)acetamide;

D-27b: 2-(1-Azabicyclo[2.2.2]oct-3-yl)-N-(6-bromo-1-benzothien-2-yl)acetamide;

D-27c: 2-(1-Azabicyclo[2.2.2]oct-3-yl)-N-(7-quinolinyl)acetamide;

D-27d: 2-(1-Azabicyclo[2.2.2]oct-3-yl)-N-(2-naphthyl)acetamide;

D-27e: 2-(1-Azabicyclo[2.2.2]oct-3-yl)-N-(8-nitro-2-naphthyl)acetamide;

D-28a: N-(1-Azabicyclo[2.2.2]oct-3-yl)-6-quinolinecarboxamide;

D-28b: N-(1-Azabicyclo[2.2.2]oct-3-yl)-2-phenazinecarboxamide;

D-28c: N-(1-Azabicyclo[2.2.2]oct-3-yl)-7-quinolinecarboxamide;

D-28d: N-[(3R)-1-Azabicyclo[2.2.2]oct-3-yl]-6-quinolinecarboxamide;

D-28e: N-(1-Azabicyclo[2.2.2]oct-3-yl)-2-ethyl-7-quinolinecarboxamide;

D-28f: N-(1-Azabicyclo[2.2.2]oct-3-yl)-2-ethyl-6-quinolinecarboxamide;

D-28g: N-(1-Azabicyclo[2.2.2]oct-3-yl)-2-methyl-7-quinolinecarboxamide;

D-28h: N-(1-Azabicyclo[2.2.2]oct-3-yl)-2-methyl-6-quinolinecarboxamide;

D-28i: N-(1-Azabicyclo[2.2.2]oct-3-yl)-4-methyl-6-quinolinecarboxamide;

D-28j: N-(1-Azabicyclo[2.2.2]oct-3-yl)-2-propyl-6-quinolinecarboxamide;

D-28k: N-(1-Azabicyclo[2.2.2]oct-3-yl)-2-ethyl-4-methyl-6-quinolinecarboxamide;

D-28l: N-(1-Azabicyclo[2.2.2]oct-3-yl)-2-propyl-7-quinolinecarboxamide;

D-28m: N-(1-Azabicyclo[2.2.2]oct-3-yl)-2-ethyl-4-methyl-7-quinolinecarboxamide;

D-28n: N-(1-Azabicyclo[2.2.2]oct-3-yl)-4-(tetrahydro-2H-pyran-2-yl)-6-quinolinecarboxamide;
D-28o: N-(1-Azabicyclo[2.2.2]oct-3-yl)-4-(tetrahydro-2H-pyran-2-yl)-7-quinolinecarboxamide;
D-28p: N-(1-Azabicyclo[2.2.2]oct-3-yl)-2-phenyl-6-quinolinecarboxamide;
D-28q: N-(1-Azabicyclo[2.2.2]oct-3-yl)-2-phenyl-7-quinolinecarboxamide;
D-29: (R)-7-chloro-N-(quinuclidin-3-yl)benzo[b]thiophene-2-carboxamide;
D-30a: 5-{5-[(endo)-8-azabicyclo[3.2.1]octan-3-yloxy]pyridin-2-yl}-1H-indole;
D-30b: 5-{5-[(exo)-8-azabicyclo[3.2.1]octan-3-yloxy]pyridin-2-yl}-1H-indole;
D-30c: 5-{5-[(endo)-8-methyl-8-aza-bicyclo[3.2.1]oct-3-yloxy]pyridin-2-yl}-1H-indole;
D-30d: 5-{5-[(exo)-8-methyl-8-aza-bicyclo[3.2.1]oct-3-yloxy]pyridin-2-yl}-1H-indole; D-30e: 4-{5-[(exo)-8-methyl-8-aza-bicyclo[3.2.1]oct-3-yloxy]pyridin-2-yl}-1H-indole; and
D-30f: 5-{6-[(exo)-8-methyl-8-aza-bicyclo[3.2.1]oct-3-yloxy]pyridin-3-yl}-1H-indole;
wherein each of said compound is in free base form or in acid addition salt form.

In one embodiment, the α7-nAChR agonist is a compound selected from the group consisting of compound A-1, A-2 and A-3; wherein each of said compound is in free base form or in acid addition salt form.

In one embodiment, the α7-nAChR agonist is a compound selected from the group consisting of compound B-1, B-2, B-3, B-4, B-5, B-6, B-7, B-8, B-9, B-10, B-11, B-12, B-13, B-14, B-15, B-16, B-17, B-18, B-19, B-20 and B-21; wherein each of said compound is in free base form or in acid addition salt form.

In one embodiment, the α7-nAChR agonist is compound B-5, which is in free base form or in acid addition salt form. In another embodiment, the α7-nAChR agonist is compound B-5, which is in fumarate salt form. In yet another embodiment, the α7-nAChR agonist is the mono-fumarate salt of compound B-5.

In one embodiment, the α7-nAChR agonist is a compound selected from the group consisting of compound C-1, C-2, C-3, C-4, C-5, C-6, C-7, C-8, C-9, C-10, C-11 and C-12; wherein each of said compound is in free base form or in acid addition salt form.

In one embodiment, the α7-nAChR agonist is a compound selected from Group P2; Group P2 is the group consisting of compounds A-1, A-2, A-3, B-1, B-2, B-3, B-4, B-5, B-6, B-7, B-8, B-9, B-10, B-11, B-12, B-13, B-14, B-15, B-16, B-17, B-18, B-19, B-20, B-21, C-1, C-2, C-3, C-4, C-5, C-6, C-7, C-8, C-9, C-10, C-11, C-12, D-1, D-1a, D-1b, D-1c, D-1d, D-2, D-3, D-3a, D-4, D-4a, D-8, D-8a, D-8b, D-9, D-9a, D-9b, D-10, D-10a, D-11, D-11a, D-11b, D-11c, D-11d, D-11e, D-12, D-19, D-22, D-24, D-24a, D-24b, D-25a, D-25b, D-25c, D-25d, D-25e, D-25f, D-25g, D-25h, D-25i, D-25j, D-25k, D-25l, D-25m, D-25n, D-25o, D-25p, D-25q, D-25r, D-25s, D-25t, D-25u, D-25v, D-28a, D-28b, D-28c, D-28d, D-28e, D-28f, D-28g, D-28h, D-28i, D-28j, D-28k, D-28l, D-28m, D-28n, D-28o, D-28p, D-28q D-29, D-30a, D-30b, D-30c, D-30d, D-30e and D-30f; wherein each of said compound is in free base form or in acid addition salt form.

In one embodiment, the α7-nAChR agonist is a compound selected from Group P3; Group P3 is the group consisting of compounds A-1, A-2, A-3, B-1, B-2, B-3, B-4, B-5, B-6, B-7, B-8, B-9, B-10, B-11, B-12, B-13, B-14, B-15, B-16, B-17, B-18, B-19, B-20, B-21, C-1, C-2, C-3, C-4, C-5, C-6, C-7, C-8, C-9, C-10, C-11, C-12, D-1, D-1a, D-1b, D-1c, D-1d, D-2, D-3, D-3a, D-4, D-4a, D-8, D-8a, D-8b, D-9, D-9a, D-9b, D-10, D-10a, D-11, D-11a, D-12, D-19, D-22, D-24, D-24a, D-24b D-29, D-30a, D-30b, D-30c, D-30d, D-30e and D-30f; wherein each of said compound is in free base form or in acid addition salt form.

In one embodiment, the α7-nAChR agonist is a compound selected from Group P4; Group P4 is the group consisting of compounds A-1, B-5, B-8, B-12, B-13, C-5, C-6 and C-8; wherein each of said compounds is in free base form or in acid addition salt form.

The compounds of formula (I) (e.g. compounds A-1 to A-3, B-1 to B-21 and C-1 to C-12) and their manufacture are known from WO2001/85727, WO2004/022556, WO2005/123732, WO2006/005608, WO2007/045478, WO2007/068476 and WO2007/068475, or can be prepared analogously to said references.

Compounds D-1 and D-1a can be prepared according to WO2008/058096.

Compounds D-2, D-3, D-3a, D-4, D-4a and D-5 (A-582941) can be prepared according to WO2005/028477. Compounds D-6, D-6a, D-7 and E7a can be prepared according to WO2006/065233 and/or WO2007/018738. Compounds D-8, D-8a, D-8b, D-9, D-9a and D-9b can be prepared according to WO2004/029050 and/or WO2010/043515.

Compounds D-10 and D-10a can be prepared according to WO2004/076449 and/or WO2009/018505. Compounds D-11, D-11a to D-11e can be prepared according to WO2004/076449 and/or WO2010/085724 and/or WO2010/056622. Compounds D-12 (CP-810123) and Compound D-19 (varenicline) are described in O'Donnell et al, J Med Chem, 2010, 53, 1222-1237. Compounds D-13 (PNU-282987), D-14 (PHA543613), D-21 (SSR-180771) and D-23 (ABBF) are described in Horenstein et al, Mol Pharmacol, 2008, 74, 1496-1511. Compounds D-15 (PHA568487), D-16 (WAY-317538), D-17 (WAY-264620), D-20 (AZD-0328) and D-22 (GTS-21) are described in Haydar et al, Current Topics in Medicinal Chemistry, 2010, 10, 144-152. Compound D-18 (WYE-103914) is described in Ghiron et al, J Med Chem, 2010, 53, 4379-4389. Compound D-24, D-24a and D-24b are described in WO2007/133155 and/or WO2009/066107. Compounds D-25a to D-25v are described in WO2004/013136. Compounds D-26a to D-26z are described in WO2003/078431. Compounds D-27a to D-27e are described in WO2003/078430. Compounds D-28a to D-28q are described in WO2003/043991. Compound D-29 is described in WO2003/055878. Compounds D-30a to D-30f are described in WO2007/137030.

LMW α7-nAChR Positive Allosteric Modulators:
In One Embodiment, the α7-nAChR Activator Used is an α7-nAChR Positive Allosteric Modulator.

As used herein a "α7-nAChR positive allosteric modulator" is a compound that binds to a receptor comprising an α7-nAChR subunit in vivo and in vitro and is potentiating the activation of the receptor when its physiological ligand (i.e. acetylcholine) is binding. Potentiation can be measured by the method disclosed in WO2001/85727, i.e. a functional affinity assay at the homomeric α7-nAChR carried out with a rat pituitary cell line stably expressing the α7-nAChR. As read out, the calcium influx upon stimulation of the receptor compared to acetylcholine-binding alone is used. "α7-nAChR positive allosteric modulators" according to the invention typically induce calcium influx of at least 200% of the maximal influx evoked by acetylcholine with an $EC_{50}$ value of at least 5000 nM; preferred α7-nAChR positive allosteric modulater induce calcium influx of at least 300% of the maximal influx evoked by acetylcholine with an $EC_{50}$ value of at least 1000 nM; more preferred agonists induce calcium influx of at least 400% of the maximal influx evoked by epibatidine with an $EC_{50}$ value of at least 500 nM.

In particular, preferred α7-nAChR positive allosteric modulators should be well absorbed from the gastrointestinal tract, should be sufficiently metabolically stable and possess favorable pharmacokinetic properties.

Further preferred α7-nAChR positive allosteric modulators bind in-vivo potently to α7-nAChRs whilst showing little affinity for other receptors, especially for other nAChRs, e.g. α4β2 nAChR, for muscarinic acetylcholine receptors, e.g. M1, and/or the 5-$HT_3$ receptor. Further preferred α7-nAChR positive allosteric modulators cross the blood brain barrier effectively.

Preferred α7-nAChR positive allosteric modulators should be non-toxic and demonstrate few side-effects.

Furthermore, a preferred α7-nAChR positive allosteric modulator will be able to exist in a physical form that is stable, non-hygroscopic and easily formulated.

In one embodiment, the α7-nAChR positive allosteric modulator is a selective α7-nAChR positive allosteric modulator, i.e. is selective for a receptor comprising an α7-nAChR subunit, since such a positive allosteric modulator would be expected to cause fewer side effects than a non-selective positive allosteric modulator to a treated subject. A positive allosteric modulator being selective for a receptor comprising an α7-nAChR subunit has a functional affinity to such a receptor to a much higher degree, e.g. at least 10-fold affinity difference in $EC_{50}$ value, preferably at least 20-fold, more preferably at least 50-fold, compared to any other nicotinic acetylcholine receptor. To assess the affinity of the α7-nAChR positive allosteric modulator of the invention on other nicotinic acetylcholine receptors, the method disclosed in WO2001/85727 can be used, i.e. to assess the affinity on human neuronal α4β2 nAChR, a similar functional assay is carried out using a human embryonic kidney cell line stable expressing the human α4β2 subtype and to assess the activity of the compounds of the invention on the "ganglionic subtype" and the "muscle type" of nicotinic receptor, similar functional assays are carried out with a human embryonic kidney cell line stably expressing the human "ganglionic subtype" or a cell line endogenously expressing the human "muscle type" of nicotinic receptors.

In the last 12 years much effort has been focused on developing selective α7 nAChR positive allosteric modulators leading to the discovery of many different chemotypes displaying said selective activity. These efforts are summarized the review from Haydar et al (Current Topics in Medicinal Chemistry, 2010, 10, 144-152), which describes 11 compounds acting as α7 nAChR positive allosteric modulators belonging to seven different chemical families; i.e. XY-4083; PNU-120596, PHA-758454 and NS-1738; PHA-709829; SB-206553; LY-2087101, LY-1078733 and LY-2087133; compound 26; and A-867744 (compound designations taken from Haydar et al). All said 11 compounds described in Haydar et al are incorporated herein by reference. In fact, at least one drug candidate having an α7 nAChR positive allosteric modulator mode of action obtained permission from the U.S. Food and Drug Administration to conduct clinical testing (i.e. XY-4083).

In one embodiment, the α7-nAChR positive allosteric modulator has a maximum molecular weight of 1500 daltons. In one embodiment, the α7-nAChR positive allosteric modulator has a maximum molecular weight of 1000 daltons. In one embodiment, the α7-nAChR positive allosteric modulator has a maximum molecular weight of 800 daltons. In one embodiment, the α7-nAChR positive allosteric modulator has a maximum molecular weight of 500 daltons.

In one embodiment, the α7-nAChR positive allosteric modulator is a compound selected from the Group P5; Group P5 is the group consisting of compounds E-1: (Z)—N-(4-Chloro-phenyl)-3-(4-chloro-phenylamino)-2-(3-methyl-isoxazol-5-yl)-acrylamide (XY-4083);

E-2: 1-(5-Chloro-2,4-dimethoxy-phenyl)-3-(5-methyl-isoxazol-3-yl)-urea (PNU-120596);

E-3: 1-(5-Fluoro-2,4-dimethoxy-phenyl)-3-(5-trifluoromethyl-isoxazol-3-yl)-urea (PHA-758454);

E-4: 1-(5-Chloro-2-hydroxy-phenyl)-3-(2-chloro-5-trifluoromethyl-phenyl)-urea (NS-1738);

E-5: 4-(4-Chloro-phenyl)-2-(4-methoxy-phenyl)-5-methyl-2H-pyrazol-3-ylamine (PHA-709829);

E-6: 5-Methyl-3,5-dihydro-2H-pyrrolo[2,3-f]indole-1-carboxylic acid pyridin-3-ylamide (SB-206553);

E-7: [2-(4-Fluoro-phenylamino)-4-methyl-thiazol-5-yl]-thiophen-3-yl-methanone (LY-2087101);

E-8: [2-(4-Fluoro-phenylamino)-4-methyl-thiazol-5-yl]-p-tolyl-methanone (LY-1078733);

E-9: Benzo[1,3]dioxol-5-yl-[2-(4-fluoro-phenylamino)-4-methyl-thiazol-5-yl]-methanone (LY-2087133);

E-10: 4-Naphthalen-1-yl-3a,4,5,9b-tetrahydro-3H-cyclopenta[c]quinoline-8-sulfonic acid amide; and E-11: 4-[5-(4-Chloro-phenyl)-2-methyl-3-propionyl-pyrrol-1-yl]-benzenesulfonamide (A-867744); wherein said compound is in free base form or in acid addition salt form.

In yet another embodiment, the above disclosed compositions comprising an alpha 7 nicotinic acetylcholine receptor activator for the treatment of cognitive impairments, psychotic and/or neurodegenerative disorders in a group of patients selected according to the herein disclosed methods, comprises a second cognition enhancer or therapeutic compound, such as a conventional antipsychotic or an atypical antipsychotic.

In one embodiment the invention provides methods for predicting therapeutic responsiveness of a subject, e.g. a human subject, to alpha 7 nicotinic acetylcholine receptor activator treatment, based on the presence or absence of particular genetic markers in the subject to be treated. The term "predicting therapeutic responsiveness to alpha 7 nicotinic acetylcholine receptor activator treatment", as used herein, is intended to refer to an ability to assess the likelihood that treatment of a subject with an alpha 7 nicotinic acetylcholine receptor activator will or will not be clinically effective in (e.g., provide a measurable benefit to) the subject. In particular, such an ability to assess the likelihood that treatment will or will not be clinically effective is typically exercised before treatment with the alpha 7 nicotinic acetylcholine receptor activator is begun in the subject. However, it is also possible that such an ability to assess the likelihood that treatment will or will not be clinically effective can be exercised after treatment has begun but before an indicator of clinical effectiveness (e.g. an indicator of measurable benefit) has been observed in the subject.

The method comprises the steps of: I) obtaining the genotype of the individual at the genetic locus of the CYP1A2 gene; II) identifying those individuals of step I. carrying the CYP1A2 SNP rs2069514-A (SEQ ID NO. 1) or the SNP rs2069514-G (SEQ ID NO. 2) or a SNP forming a haplotype with said SNPs, wherein the homozygous presence of the CYP1A2 SNP rs2069514-A/A or SNP haplotype, or heterozygous presence of the CYP1A2 SNP rs2069514-A/G or SNP haplotype, is an indication that the individual will likely respond to the alpha 7 nicotinic acetylcholine receptor activator treatment.

Characterization of the CYP1A2 and/SNPs or obtaining genotype information of an individual at said loci may be accomplished by using any of the techniques well known in the art. For example, any of the regions of the genes may be sequenced. Any of the well-known methods for sequencing one or both strands of the CYP1A2 gene may be used in the methods of the invention, such as the methods described in, for example, U.S. Pat. No. 5,075,216, Engelke et al. (1988) *Proc. Natl. Acad. Sci. U.S.A.* 85, 544-548 and Wong et al. (1987) *Nature* 330, 384-386; Maxim and Gilbert (1977) *Proc. Natl. Acad. Sci. U.S.A.* 74:560; or Sanger (1977)*Proc. Natl. Acad. Sci. U.S.A.* 74:5463. In addition, any of a variety of automated sequencing procedures can be utilized see, e.g., Naeve, C. W et al. (1995) *Biotechniques* 19:448, including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159.

Determining the presence or absence of an CYP1A2 SNPs in a biological sample may be accomplished using any well known technique such as polymerase chain reaction (PCR) amplification reaction, reverse-transcriptase PCR analysis, single-strand conformation polymorphism analysis (SSCP), mismatch cleavage detection, heteroduplex analysis, Southern blot analysis, Western blot analysis, deoxyribonucleic acid sequencing, restriction fragment length polymorphism analysis, haplotype analysis, serotyping, and combinations or sub-combinations thereof.

For example, a mRNA sample may be obtained from the subject and expression of mRNA(s) encoded by the CYP1A2 allele in the mRNA sample may be detected using standard molecular biology techniques, such as PCR analysis. A preferred method of PCR analysis is reverse transcriptase-polymerase chain reaction (RT-PCR). Other suitable systems for mRNA sample analysis include microarray analysis (e.g., using Affymetrix's microarray system or Illumina's BeadArray Technology).

In certain situations it may be possible to assay for the expression of an indicative marker allele of the CYP1A2 gene at the protein level, using a detection reagent that detects the protein product encoded by the mRNA of the biomarker. For example, if an antibody reagent is available that binds specifically to the CYP1A2 marker protein, and not to other proteins, then such an antibody can be used to detect the expression of the CYP1A2 marker protein in a cellular sample from the subject, or a preparation derived from the cellular sample, using standard antibody-based techniques known in the art, such as FACS analysis, ELISA and the like.

As indicated above, determining the presence or absence of an indicative marker allele of the CYP1A2 gene may include, for example, restriction fragment length polymorphism analysis. Restriction fragment length polymorphism analysis (RFLPS) is based on changes at a restriction enzyme site. Moreover, the use of sequence specific ribozymes (see, for example, U.S. Pat. No. 5,498,531) may be used to score for the presence of a specific ribozyme cleavage site.

Another technique for determining the presence or absence of an indicative marker allele of the CYP1A2 gene or a SNP forming a haplotype with such an indicative allele involves hybridizing DNA segments which are being analyzed (target DNA) with a complimentary, labeled oligonucleotide probe as described in, for example, Wallace et al. (1981) *Nucl. Acids Res.* 9, 879-894. Since DNA duplexes containing even a single base pair mismatch exhibit high thermal instability, the differential melting temperature may be used to distinguish target DNAs that are perfectly complimentary to the probe from target DNAs that only differ by a single nucleotide. This method has been adapted to detect the presence or absence of a specific restriction site, as described in, for example, U.S. Pat. No. 4,683,194. The method involves using an end-labeled oligonucleotide probe spanning a restriction site which is hybridized to a target DNA. The hybridized duplex of DNA is then incubated with the restriction enzyme appropriate for that site. Reformed restriction sites will be cleaved by digestion in the pair of duplexes between the probe and target by using the restriction endonuclease. The specific restriction site is present in the target DNA if shortened probe molecules are detected.

Other methods for determining the presence or absence of an indicative marker allele of the CYP1A2 gene or a SNP forming a haplotype with such an indicative allele include methods in which protection from cleavage agents is used to detect mismatched bases in RNA/RNA or RNA/DNA heteroduplexes (as described in, for example, Myers et al. (1985) *Science* 230:1242). In general, the art technique of "mismatch cleavage" starts by providing heteroduplexes formed by hybridizing (labeled) RNA or DNA containing the polymorphic sequence with potentially polymorphic RNA or DNA obtained from a sample. The double-stranded duplexes are treated with an agent which cleaves single-stranded regions of the duplex such as which will exist due to base-pair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels. See, for example, Cotton et al. (1988) *Proc. Natl Acad Sci USA* 85:4397; Saleeba et al. (1992) *Methods Enzymol.* 217:286-295. In a preferred embodiment, the control DNA or RNA can be labeled for detection.

In another embodiment, alterations in electrophoretic mobility may be used to determine the presence or absence of an indicative marker allele of the CYP1A2 gene or a SNP forming a haplotype with such an indicative allele. For example, single strand conformation polymorphism (SSCP) may be used to detect differences in electrophoretic mobility between various indicative marker allele of the CYP1A2 gene or a SNP forming a haplotype with such an indicative allele (as described in, for example, Orita et al. (1989) Proc Natl. Acad. Sci. USA: 86:276; Cotton (1993) Mutat Res 285:125-144; and Hayashi (1992) Genet Anal Tech Appl 9:73-79). Single-stranded DNA fragments of sample and control nucleic acids can be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the movement of a nucleic acid molecule in polyacrylamide gels containing a gradient of denaturant is assayed using denaturing gradient gel electrophoresis (DGGE) (as described in, for example, Myers et al. (1985) Nature 313:495. When DGGE is used as the method of analysis, DNA can be modified to ensure that it does not completely denature, for example by adding a GC clamp of approximately 40 bp, of high-melting GC-rich DNA by PCR. In a further embodiment, a temperature gradient is used in place of a denaturing gradient to identify differences in the mobility of control and sample DNA (Rosenbaum and Reissner (1987) Biophys Chem 265: 12753).

Examples of other techniques for determining the presence or absence of an indicative marker allele of the CYP1A2 gene or a SNP forming a haplotype with such an indicative allele include, but are not limited to, selective oligonucleotide hybridization, selective amplification, or selective primer extension. For example, oligonucleotide primers may be prepared in which the polymorphic region is placed centrally and then hybridized to target DNA under conditions which permit hybridization only if a perfect match is found (Saiki et al. (1986) Nature 324:163; Saiki et al. (1989) Proc. Natl. Acad. Sci. USA 86:6230). Such allele specific oligonucleotides are hybridized to PCR amplified target DNA or a number of different polymorphisms when the oligonucleotides are attached to the hybridizing membrane and hybridized with labeled target DNA.

Another process for determining the presence or absence of an indicative marker allele of the CYP1A2 gene or a SNP forming a haplotype with such an indicative allele is the primer extension process which consists of hybridizing a labeled oligonucleotide primer to a template RNA or DNA and then using a DNA polymerase and deoxynucleoside triphosphates to extend the primer to the 5' end of the template. Resolution of the labeled primer extension product is then done by fractionating on the basis of size, e.g., by electrophoresis via a denaturing polyacrylamide gel. This process is often used to compare homologous DNA segments and to detect differences due to nucleotide insertion or deletion. Differences due to nucleotide substitution are not detected since size is the sole criterion used to characterize the primer extension product. Additional well known methods for SNP genotyping are:

Dynamic allele-specific hybridization (DASH) genotyping (Howell W., Jobs M., Gyllensten U., Brookes A. (1999) Dynamic allele-specific hybridization. A new method for scoring single nucleotide polymorphisms. Nat Biotechnol. 17(1):87-8).

SNP detection through molecular beacons (Abravaya K., Huff J., Marshall R., Merchant B., Mullen C., Schneider G., and Robinson J. (2003) Molecular beacons as diagnostic tools: technology and applications. Clin Chem Lab Med. 41:468-474).

High-density oligonucleotide SNP micrarrays (Rapley R., Harbron S. (Eds.) (2004) Molecular Analysis and Genome Discovery. Chichester. John Wiley & Sons Ltd.).

Flap endonucleases (The Invader assay for SNP genotyping. Mutat Res. 573(1-2):103-10).

In the event that a SNP is located in the promoter region, or another non-coding region having influence on the expression rate of the gene carrying said SNP, the mRNA or protein levels might be affected. In such a situation, the presence of a SNP cannot be determined on the basis of the mRNA or protein sequence of said respective gene. However presence of such an indicative SNP could be determined indirectly by mRNA or Protein levels measurements. Hence, in another embodiment of the invention, the herein disclosed methods can comprise an additional or alternative step of determining the mRNA or protein level of a certain gene or gene product as an indirect determination method for the presence of an indicative SNP in the CYP1A2 gene.

Haplotype analysis of one or more polymorphic sites around an indicative marker allele or SNP of the CYP1A2 gene may also be used for determining the presence or absence of additional indicative SNPs and may include, for example, use of family pedigrees, molecular techniques and/or statistical inference.

Moreover, any of the well-known methods for genotyping such SNPs (e.g., DNA sequencing, hybridisation techniques, PCR based assays, fluorescent dye and quenching agent-based PCR assay (Taqman PCR detection system), RFLP-based techniques, single strand conformational polymorphism (SSCP), denaturating gradient gel electrophoresis (DGGE), temperature gradient gel electrophoresis (TGGE), chemical mismatch cleavage (CMC), heteroduplex analysis based system, techniques based on mass spectroscopy, invasive cleavage assay, polymorphism ratio sequencing (PRS), microarrays, a rolling circle extension assay, HPLC-based techniques, DHPLC-based techniques, oligonucleotide extension assays (OLA), extension based assays (ARMS, (Amplification Refractory Mutation System), ALEX (Amplification Refractory Mutation Linear Extension), SBCE (Single base chain extension), a molecular beacon assay, invader (Third wave technologies), a ligase chain reaction assay, 5'-nuclease assay-based techniques, hybridization capillary array electrophoresis (CAE), pyrosequencing, protein truncation assay (PTT), immunoassays, haplotype analysis, and solid phase hydridization (dot blot, reverse dot blot, chips) are very well known in the art and described in, for example, Siitari, Nucleic acid diagnostics market, Technology Review 125/2002, ISDN 1239-758; Caplin (1999) Biochemica 1:5-8; Neville, (2002) BioTechniques 32:34-43; Underhill (197) Genome Res 7:996-1005; Oefner (2000) J Chromatogr B Biomed Sci Appl 739:345-55, and the patent publication No. U.S. 20010049586 and may be used in the methods of the invention.

Any suitable tissue sample obtained by biopsy or otherwise from the a subject afflicted with cognitive impairments, psychotic and/or neurodegenerative disorders may be used to determine the presence or absence of an indicative marker allele of the CYP1A2 gene or a SNP forming a haplotype with such an indicative allele. Techniques or methods for obtaining a biopsy from a subject are well known in the art. Isolating sub-components of tissue samples (e.g., cells or RNA or DNA) may be accomplished using well known techniques in the art and those described in the Examples section below.

The presence, particularly the homozygous presence of the CYP1A2 SNP rs2069514-A/A (SEQ ID NO. 1) in combination with the heterozygous CYP1A2 SNP rs2069514-A/G or a SNP forming a haplotype with said SNPs is an indication that the individual will likely respond to the herein described alpha 7 nicotinic acetylcholine receptor activator treatment. The homozygous presence of the SNP rs2069514-G/G (SEQ ID NO. 2) is an indication that the individual will likely not respond to the alpha 7 nicotinic acetylcholine receptor activator treatment.

Hence, the disclosure also relates to a therapeutic method of increasing the cognitive skills of an individual and/or treatment of individuals suffering from a cognitive impairment, psychotic and/or neurodegenerative disorder comprising the steps of: III) obtaining the genotype of the individual at the genetic locus of the CYP1A2 gene as described above; IV) identifying those individuals of step III) carrying the CYP1A2 SNP rs2069514-A (SEQ ID NO. 1) or the SNP rs2069514-G (SEQ ID NO. 2), or a SNP forming a haplotype with said SNPs or a SNP in the same linkage disequilibrium with said SNPs, wherein the homozygous presence of the CYP1A2 SNP rs2069514-A/A or corresponding SNP haplotype, or heterozygous presence of the CYP1A2 SNP rs2069514-A/G or corresponding SNP haplotype is an indication that the individual will likely respond to the alpha 7 nicotinic acetylcholine receptor activator treatment V) administering a therapeutic effective amount of an alpha 7 nicotinic acetylcholine receptor activator to those subject identified in step IV).

In an additional embodiment, the above described steps I) and III) further comprising the steps of: VI) obtaining a biological sample of said individual, wherein said sample is selected from the group consisting of blood, blood-derived product (such as buffy coat, serum, and plasma), lymph, urine, tear, saliva, cerebrospinal fluid, buccal swabs, sputum, hair roots, leukocyte sample or tissue samples or any combination thereof, and VII) contacting the biological sample of step VI) with a reagent or agent capable of detecting (as described in detail above) the (i) CYP1A2 SNP rs2069514-A (SEQ ID NO. 1), or (ii) the CYP1A2 SNP rs2069514-G (SEQ ID NO. 2), or (iii) a SNP forming a haplotype with said SNPs or a SNP in the same linkage disequilibrium with said SNPs.

The reagent, agent or device with which the biological sample is contacted may be, for example, a PCR/sequencing primer(s), nucleotides and enzymes suitable for amplifying and/or sequencing and/or labeling the CYP1A2 SNP rs2069514-A (SEQ ID NO. 1), or (ii) the CYP1A2 SNP rs2069514-G (SEQ ID NO. 2) or a SNP forming a haplotype with said SNPs or a SNP in the same linkage disequilibrium with said SNPs present in the sample, an antibody capable of detecting one of the above mentioned SNPs or a SNP forming a haplotype with said SNPs or a SNP in the same linkage disequilibrium with said SNPs in the sample, a restriction enzyme, and/or a microarray.

The term "therapeutically effective amount" in the context of administering an therapeutically effective amount as used herein typically refers to an amount of an active ingredient (e.g. alpha 7 nicotinic acetylcholine receptor activator and/or second cognition enhancer as described herein) which, when administered to a subject, is sufficient to provide a therapeutic benefit, e.g. is sufficient for treating cognitive impairments or dysfunctions, psychotic and/or neurodegenerative disorders, particularly for increasing the cognitive skills of an individual. In another aspect of the invention, the cognitive impairments or dysfunctions, psychotic and/or neurodegenerative disorders is a mental disease or a acquired deficit in one or more of memory function, problem solving, orientation and/or abstraction, particularly pronounced in verbal memory, executive functions, attention and vigilance, verbal fluency and motor speed. In an additional embodiment the cognitive impairments or dysfunctions, psychotic and/or neurodegenerative disorders is a mild cognitive impairment, Alzheimer's disease, Parkinson's disease dementia, dementia with Lewy Bodies, schizophrenia, vascular dementia, AIDS-dementia, senile dementia, mild cognitive impairment related to age (MCI), age associated memory impairment, autism, dementias in frontal lobe degenerations, stroke, basal ganglia degenerative disorders, multiple sclerosis, trauma, brain tumors, brain infections, hydrocephalus, depression, toxic or metabolic disorders and drug induced dementias.

Administration of an alpha 7 nicotinic acetylcholine receptor activator refers to the administration of an alpha 7 nicotinic acetylcholine receptor-agonist or -positive allosteric modulators, particularly to low molecular weight compounds being selected from group P1. Alternatively, the therapeutic method of increasing the cognitive skills of an individual and/or treatment of individuals suffering from a cognitive impairment, psychotic and/or neurodegenerative disorder comprises the step of administering the alpha 7 nicotinic acetylcholine receptor agonist as disclosed in formula (I), or a compound selected from the group P1.

"Pharmaceutically acceptable salts" are known in the field (e.g. S. M. Berge, et al, "Pharmaceutical Salts", J. Pharm. Sd., 1977, 66:1-19; and "Handbook of Pharmaceutical Salts, Properties, Selection, and Use", Stahl, R H., Wermuth, C. G., Eds.; Wiley-VCH and VHCA: Zurich, 2002). A pharmaceutically acceptable salt is intended to mean a salt of a free form that is not toxic, biologically intolerable, or otherwise biologically undesirable. Preferred pharmaceutically acceptable salts are those that are pharmacologically effective and suitable for contact with the tissues of patients without undue toxicity, irritation, or allergic response.

In yet another embodiment, in the disclosed methods of treatment a second cognition enhancer or a therapeutic compound useful for the treatment of cognitive impairments, psychotic and/or neurodegenerative disorders, such as a conventional antipsychotic or an atypical antipsychotic, can be administered. Preferably, a combination being a pharmaceutical composition or a combined pharmaceutical preparation is used. Such a pharmaceutical composition can be administered together, one after the other or separately in one combined unit dosage.

In another aspect of the disclosed methods, the alpha 7 nicotinic acetylcholine receptor activator dose to be administered is from about 1 mg to about 100 mg per day. Alternatively, the dose to be administered is from about 2 mg to about 100 mg, or about 3 mg to about 90 mg, or about 4 mg to about 80 mg, or about 5 mg to about 70 mg, or about 6 mg to about 60 mg, or about 7 mg to about 50 mg, or about 8 mg to about 40 mg, or about 9 mg to about 35 mg, or about 10 mg to about 30 mg per day, or about 5 mg to about 10 mg, or about 10 mg to about 15 mg, or about 15 mg to about 20 mg, or about 20 mg to about 25 mg per day. In one embodiment of said aspects, the alpha 7 nicotinic acetylcholine receptor activator is an alpha 7 nicotinic acetylcholine receptor agonist.

Another embodiment of the disclosure relates to the use of an alpha 7 nicotinic acetylcholine receptor activator as described above for the treatment of a patient with cognitive impairments, psychotic and/or neurodegenerative disorders or condition in which alpha 7 nicotinic acetylcholine receptor activation plays a role or is implicated, wherein the patient being susceptible for the treatment with an alpha 7 nicotinic acetylcholine receptor activator has been selected according to the above described methods.

Furthermore, the disclosure relates to the use of at least one probe for detecting the (i) the SNP rs2069514-A (SEQ ID NO. 1), or (ii) the SNP rs2069514-G (SEQ ID NO. 2), or (iii) a SNP forming a haplotype with said SNPs or a SNP in the same linkage disequilibrium with said SNPs for determining whether an individual is responsive to (a) the treatment of cognitive impairments, psychotic and/or neurodegenerative disorders or condition in which alpha 7 nicotinic acetylcholine receptor activation plays a role or is implicated, or (b) the increase of cognitive skills by an alpha 7 nicotinic acetylcholine receptor activator. The skilled person is aware of methods and techniques how to design usable probes.

In another aspect, the disclosure relates to a kit comprising at least one probe for detecting the (i) the SNP rs2069514-A (SEQ ID NO. 1), or (ii) the SNP rs2069514-G (SEQ ID NO. 2), or (iii) a SNP forming a haplotype with said SNPs or a SNP in the same linkage disequilibrium with said SNPs. Preferably, said kit is a kit for diagnosing a responsiveness of an individual to the treatment of cognitive impairments, psychotic and/or neurodegenerative disorders or condition in which alpha 7 nicotinic acetylcholine receptor activation plays a role or is implicated by an alpha 7 nicotinic acetylcholine receptor activator, comprising VIII) means for detecting the (i) the SNP rs2069514-A (SEQ ID NO. 1), or (ii) the SNP rs2069514-G (SEQ ID NO. 2), or (iii) a SNP forming a haplotype with said SNPs or a SNP in the same linkage disequilibrium with said SNPs, and IX) instructions how to use said kit.

An additional subject matter of the disclosure relates to the use of a kit, preferably the above disclosed kit, suitable for any of the above described methods or uses, wherein said kit comprises at least one probe for detecting the (i) the SNP rs2069514-A (SEQ ID NO. 1), or (ii) the SNP rs2069514-G (SEQ ID NO. 2), or (iii) a SNP forming a haplotype with said SNPs or a SNP in the same linkage disequilibrium with said SNPs. In a related embodiment, the kit used as described above comprises oligonucleotide probes.

Actual dosage levels of the active agents in the pharmaceutical compositions of the present invention may be varied so as to obtain an amount of the active agent which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Administration of a "therapeutically effective dosage" of an alpha 7 nicotinic acetylcholine receptor activator comprised in the compositions of the invention can result in a decrease in severity of disease symptoms, an increase in frequency and duration of disease symptom-free periods, or a prevention of impairment or disability due to the disease affliction i.e. an improvement of cognitive skills.

A composition of the present invention can be administered by one or more routes of administration using one or more of a variety of methods known in the art. As will be appreciated by the skilled artisan, the route and/or mode of administration will vary depending upon the desired results. Routes of administration may include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition can be administered by a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g. Sustained and Controlled Release Drug Delivery Systems, J. R. Robinson, ed., Marcel Dekker, Inc., New York, 1978.

Preferred therapeutic compositions are compositions for oral or transdermal administration.

A composition for enteral or parenteral administration is, for example, a unit dosage form, such as a sugar-coated tablet, a tablet, a capsule, a suppository or an ampoule.

The unit content of active ingredients in an individual dose need not in itself constitute a therapeutically effective amount, since such an amount can be reached by the administration of a plurality of dosage units. A composition according to the invention may contain, e.g., from about 10% to about 100%, preferably from about 20% to about 60%, of the active ingredients.

If not indicated otherwise, a pharmaceutical composition according to the invention is prepared in a manner known per se, e.g. by means of conventional mixing, granulating, sugar-coating, dissolving or lyophilizing processes. In preparing a composition for an oral dosage form, any of the usual pharmaceutical media may be employed, for example water, glycols, oils, alcohols, carriers, such as starches, sugars, or microcrystalline cellulose, diluents, granulating agents, lubricants, binders, disintegrating agents and the like. Because of their ease of administration, tablets and capsules represent the most advantageous oral dosage unit forms, in which case solid pharmaceutical carriers are obviously employed.

Further Embodiments of the Invention

Embodiment 1: Composition comprising an alpha 7 nicotinic acetylcholine receptor activator for use in treatment of cognitive impairments, psychotic and/or neurodegenerative disorders in a selected patient population, wherein the patient population is selected on the basis of having at least one indicative SNP of the human cytochrome P450 1A2 (CYP1A2).

Embodiment 2: Composition according to embodiment 1, wherein the cognitive impairments, psychotic and/or neurodegenerative disorders are conditions in which alpha 7 nicotinic acetylcholine receptor activation plays a role or is implicated.

Embodiment 3: Composition according to embodiment 1 and 2, wherein the cognitive impairments, psychotic and/or neurodegenerative disorders are selected from the group consisting of mild cognitive impairment, Alzheimer's disease, Parkinson's disease dementia, dementia with Lewy Bodies, schizophrenia, vascular dementia, AIDS-dementia, senile dementia, mild cognitive impairment related to age (MCI), age associated memory impairment, autism, dementias in frontal lobe degenerations, stroke, basalganglia degenerative disorders, multiple sclerosis, trauma, brain tumors, brain infections, hydrocephalus, depression, toxic or metabolic disorders and drug induced dementias.

Embodiment 4: Composition according to embodiments 1 to 3, wherein the indicative human CYP1A2 SNP is the CYP1A2 SNP rs2069514-A (SEQ ID NO. 1) or the CYP1A2 SNP rs2069514-G (SEQ ID NO. 2) or a SNP forming a haplotype with said SNPs or a SNP in the same linkage disequilibrium with said SNPs.

Embodiment 5: Composition according to any of the embodiments 1 to 4, wherein the selected patients are homozygous for the indicative CYP1A2 SNP rs2069514-A/A (SEQ ID NO. 1) or corresponding indicative CYP1A2 SNP haplotypes, or heterozygous for the indicative CYP1A2 SNP rs2069514-A/G or corresponding indicative CYP1A2 SNP haplotypes.

Embodiment 6: Composition according to embodiments 1 to 5, wherein the alpha 7 nicotinic acetylcholine receptor activator is a compound of formula (I)

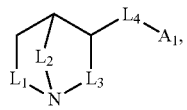

wherein
$L_1$ is —$CH_2$—; $L_2$ is —$CH_2$— or —$CH_2$—$CH_2$—; and $L_3$ is —$CH_2$— or —$CH(CH_3)$—; or
$L_1$ is —$CH_2$—$CH_2$—; $L_2$ is —$CH_2$—; and $L_3$ is —$CH_2$—$CH_2$—;
$L_4$ is a group selected from

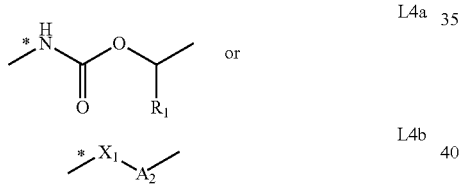

wherein the bond marked with the asterisk is attached to the azabicycloalkyl moiety;
$R_1$ is hydrogen or $C_{1-4}$alkyl;
$X_1$ is —O— or —NH—;
$A_2$ is selected from

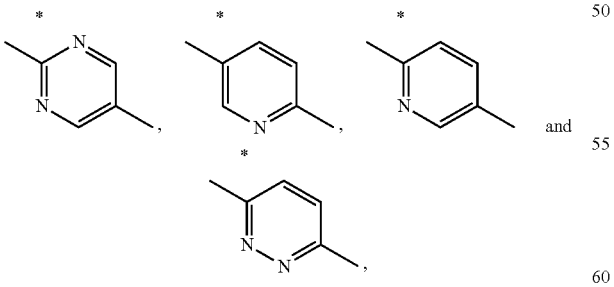

wherein the bond marked with the asterisk is attached to $X_1$;
A is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_2$, and wherein a substituent on a nitrogen in a heterocyclic ring system may not be halogen;

each $R_2$ independently is $C_{1-6}$alkyl, $C_{1-6}$halogenalkyl, $C_{1-6}$alkoxy, $C_{1-6}$halogenalkoxy, halogen, cyano or a three- to six-membered monocyclic ring system which may be aromatic, saturated or partially saturated and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;

or two $R_2$ at adjacent ring atoms form a $C_{3-4}$alkylene group, wherein 1-2 carbon atoms may be replaced by $X_2$, and wherein the $C_{3-4}$alkylene group may be substituted once or more than once by $R_3$;
each $X_2$ independently is —O— or —$N(R_4)$—;
each $R_4$ independently is hydrogen or $C_{1-6}$alkyl; and
each $R_3$ independently is halogen or $C_{1-6}$alkyl;
in free base form or in acid addition salt form.

Embodiment 7: Composition according to embodiment 6, wherein the alpha 7 nicotinic acetylcholine receptor activator is used as free base or pharmaceutically acceptable acid addition salt form.

Embodiment 8: Composition according to embodiment 7, comprising the alpha 7 nicotinic acetylcholine receptor activator in its free base or pharmaceutically acceptable acid addition salt form, in association with a pharmaceutical carrier or a diluent.

Embodiment 9: Composition according to embodiments 1 to 8, further comprising a second cognition enhancer or a therapeutic compound useful for the treatment of cognitive impairments, psychotic and/or neurodegenerative disorders.

Embodiment 10: Composition of embodiment 9, wherein the second cognition enhancer or therapeutic compound useful for the treatment of cognitive impairments, psychotic and/or neurodegenerative disorders is a conventional antipsychotic or an atypical antipsychotic.

Embodiment 11: A method for predicting therapeutic responsiveness of an individual or a group of individuals to alpha 7 nicotinic acetylcholine receptor activator treatment for increasing the cognitive skills and/or treatment of a cognitive impairment, psychotic and/or neurodegenerative disorder comprising the steps of:
I. obtaining the genotype of the individual at the genetic locus of the CYP1A2 gene; and
II. identifying those individuals of step I. carrying the CYP1A2 SNP rs2069514-A (SEQ ID NO. 1) or the SNP rs2069514-G (SEQ ID NO. 2) or a SNP forming a haplotype with said SNPs,
wherein the homozygous presence of the CYP1A2 SNP rs2069514-A/A or corresponding SNP haplotypes, or heterozygous presence of the CYP1A2 SNP rs2069514-A/G or corresponding SNP haplotypes, is an indication that the individual will likely respond to the alpha 7 nicotinic acetylcholine receptor activator treatment.

Embodiment 12: A therapeutic method of increasing the cognitive skills of an individual and/or treatment of a cognitive impairment, psychotic and/or neurodegenerative disorder comprising the steps of:
II. obtaining the genotype of the individual at the genetic locus of the CYP1A2 gene; and
IV. identifying those individuals of step III., carrying the CYP1A2 SNP rs2069514-A (SEQ ID NO. 1) or the CYP1A2 SNP rs2069514-G (SEQ ID NO. 2) or a SNP forming a haplotype with said SNPs or a SNP in the same linkage disequilibrium with said SNPs, wherein the homozygous presence of the CYP1A2 SNP rs2069514-A/A or corresponding SNP haplotypes, or heterozygous presence of the CYP1A2 SNP rs2069514-A/G or corresponding SNP haplotypes is an indication that the individual will likely respond to the alpha 7 nicotinic acetylcholine receptor activator treatment, and
V. administering a therapeutically effective amount of an alpha 7 nicotinic acetylcholine receptor activator to those subject identified in step IV.

Embodiment 13: The method according to the embodiments 11 to 12, wherein steps I or III. comprising the additional steps of
VI. obtaining a biological sample of said individual, wherein said sample is selected from the group consisting of blood, blood-derived product (such as buffy coat, serum, and plasma), lymph, urine, tear, saliva, cerebrospinal fluid, buccal swabs, sputum, hair roots, leukocyte sample or tissue samples or any combination thereof, and
VII. contacting the biological sample of step VI. with a reagent capable of detecting the (i) CYP1A2 SNP rs2069514-A (SEQ ID NO. 1), or (ii) the CYP1A2 SNP rs2069514-G (SEQ ID NO. 2), or (iii) a SNP forming a haplotype with said SNPs or a SNP in the same linkage disequilibrium with said SNPs.

Embodiment 14: A method according to the embodiments 11 to 13, further comprising as a first step the selection of patients suffering from a cognitive impairment, psychotic and/or neurodegenerative disorder.

Embodiment 15: The method according to embodiment 14, wherein the cognitive impairments, psychotic and/or neurodegenerative disorders are selected from the group consisting of mild cognitive impairment, Alzheimer's disease, Parkinson's disease dementia, dementia with Lewy Bodies, schizophrenia, vascular dementia, AIDS-dementia, senile dementia, mild cognitive impairment related to age (MCI), age associated memory impairment, autism, dementias in frontal lobe degenerations, stroke, basalganglia degenerative disorders, multiple sclerosis, trauma, brain tumors, brain infections, hydrocephalus, depression, toxic or metabolic disorders and drug induced dementias.

Embodiment 16: The method according to embodiments 11 to 15, wherein the presence of (i) the CYP1A2 SNP rs2069514-A (SEQ ID NO. 1), or (ii) the CYP1A2 SNP rs2069514-G (SEQ ID NO. 2), or (iii) a SNP forming a haplotype with said SNPs or a SNP in the same linkage disequilibrium with said SNPs is determined by using at least one oligonucleotide that specifically hybridizes with specific regions on the nucleic acid molecule carrying said SNP or SNPs.

Embodiment 17: The method according to embodiment 16, wherein the presence of said SNPs is detected by sequence-specific primer (SSP) typing, sequence-specific oligonucleotide (SSO) typing, sequence based typing (SBT), DNA amplification such as polymerase chain reaction (PCR), microarray analysis, northern blot analysis, or reverse transcription PCR.

Embodiment 18: A method of embodiments 12 to 17, wherein the alpha 7 nicotinic acetylcholine receptor activator is an alpha 7 nicotinic acetylcholine receptor activator of embodiment 6.

Embodiment 19: A method of any of the embodiments 12 to 18, wherein a second cognition enhancer or a therapeutic compound useful for the treatment of cognitive impairments, psychotic and/or neurodegenerative disorders is administered.

Embodiment 20: The method of embodiment 19, wherein the second cognition enhancer or therapeutic compound useful for the treatment of cognitive impairments, psychotic and/or neurodegenerative disorders is selected from the group of compounds listed in embodiment 10.

Embodiment 21: A method according to any one of embodiments 12 to 18, wherein the alpha 7 nicotinic acetylcholine receptor activator dose to be administered is from about 2 mg to about 100 mg per day.

Embodiment 22: Use of an alpha 7 nicotinic acetylcholine receptor activator for treatment of a patient with cognitive impairments, psychotic and/or neurodegenerative disorders or condition in which alpha 7 nicotinic acetylcholine receptor activation plays a role or is implicated, wherein the patient has been selected according to the methods of embodiments 11 to 17 as being responsive to the treatment with such an activator.

Embodiment 23: Use of at least one probe for detecting (i) the CYP1A2 SNP rs2069514-A (SEQ ID NO. 1), or (ii) the CYP1A2 SNP rs2069514-G (SEQ ID NO. 2), or (iii) a SNP forming a haplotype with said SNPs or a SNP in the same linkage disequilibrium with said SNPs for determining whether an individual is responsive to (a) the treatment of cognitive impairments, psychotic and/or neurodegenerative disorders or condition in which alpha 7 nicotinic acetylcholine receptor activation plays a role or is implicated, or (b) the increase of cognitive skills by an alpha 7 nicotinic acetylcholine receptor activator.

Embodiment 24: A kit for diagnosing a responsiveness of an individual to the treatment of cognitive impairments, psychotic and/or neurodegenerative disorders or condition in which alpha 7 nicotinic acetylcholine receptor activation plays a role or is implicated by an alpha 7 nicotinic acetylcholine receptor activator, comprising
VIII. means for detecting (i) the CYP1A2 SNP rs2069514-A (SEQ ID NO. 1), or (ii) the CYP1A2 SNP rs2069514-G (SEQ ID NO. 2), or (iii) a SNP forming a haplotype with said SNPs or a SNP in the same linkage disequilibrium with said SNPs, and
IX. instructions how to use said kit.

Embodiment 25: Use of a kit suitable for any of the methods or uses of embodiments 11 to 23, wherein said kit comprises at least one probe for detecting (i) the CYP1A2 SNP rs2069514-A (SEQ ID NO. 1), or (ii) the CYP1A2 SNP rs2069514-G (SEQ ID NO. 2), or (iii) a SNP forming a haplotype with said SNPs or a SNP in the same linkage disequilibrium with said SNPs.

Embodiment 26: The use according to any one of embodiments 22, 23 and 25 or the kit according to the embodiment 24, wherein each probe is an oligonucleotide.

Embodiment 27: The use according to the embodiments 22, 23 and 25, wherein the kit according to embodiment 24 is used.

Embodiment 28: A kit for diagnosing a responsiveness of an individual to the treatment of cognitive impairments, psychotic and/or neurodegenerative disorders or condition in which alpha 7 nicotinic acetylcholine receptor activation plays a role or is implicated by an alpha 7 nicotinic acetylcholine receptor activator, comprising means for detecting (i) the CYP1A2 SNP rs2069514-A (SEQ ID NO. 1), or (ii) the CYP1A2 SNP rs2069514-G (SEQ ID NO. 2), or (iii) a SNP forming a haplotype with said SNPs or a SNP in the same linkage disequilibrium with said SNPs.

Embodiment 29: Use of a kit suitable for any of the methods or uses of embodiments 11 to 23, wherein said kit comprises at least one probe for detecting (i) the CYP1A2 SNP rs2069514-A (SEQ ID NO. 1), or (ii) the CYP1A2 SNP rs2069514-G (SEQ ID NO. 2), or (iii) a SNP forming a haplotype with said SNPs or a SNP in the same linkage disequilibrium with said SNPs.

Embodiment 30: The use according to any one of embodiments 22, 23 and 25 or the kit according to the embodiment 28, wherein each probe is an oligonucleotide.

Embodiment 31: The use according to the embodiments 22, 23 and 25, wherein the kit according to embodiment 28 is used.

SEQUENCES

| SEQ ID NO. | SNP name | Sequence |
|---|---|---|
| 1 | CYP1A2 SNP rs2069514-A | CGAATTGTAACAAATATATTACACCACTGCAAGATGTTAATAATAGGGGAAACTGCAGA GTGGGGGTGGTAAATGGCCACTTTTACCTCCCTCATCATACTTTCCACTCAATTTTTCT GTGAACCAAAGACTGCTCTAAAAAAATCTATTAGCTTTTTAAAATTCCTTGGCTCCCCT CCAAAAAGTGTACATATGACATGATCTCATTTATGTAAAATACAACAAGCAAAACAAAT CCATGCAATAGATGTTGGGGTCATGGGTACCCTTGAGAAAGGAACACAACGGGACTT CTTGGATGCTTATGATGTCTCTTGATTAGAGCTGGTTATATGTGTGTTTGTTAAGTTTG CAAAAATTCATCAAGCTACACATGATCGAGCTATACATGACATATGCACTTTTCCATTT ATTTATTTATTTTTGAGACAGAATCTTGCTCTGTCACCCAGGCTGGAGTGCAGTGGTG CGATCTTGGCTCACCGCAACCTCCGCCTCTCAGATTCAAGCAATTGTCATGCCCCAG CTTCCCGAGTAGCTGGAATTACAGGTGTGCACCATCACGCCCAGCTAATTTTTTTTG TATTTTTAGTAGAGATGAGGTTTCACTATGTTGGCCAGGCTGGTCTTGAACTCCTGGC CTCACTCAAGTGATCCTCCCACCTCGGCCTCCCAAAGTGCTAGAATTACAGGTGTGA GTCACCGGTCCCAGCTGACATATGCACTTTTCTATATTGTATCCTGTAATTTAATTTTTT TAAGTTTTAAGAAAACATTAAAAATAAAAAGATAAATAGTCTGTCATACAGGAGAATTTC AAATAGTTTATGGAGATAATCCCCCCTCAAGGAGAAGGAGCGTAATCCCCCACTCCTT CGGTGTGGGCTGTGCATAGTGACTTCCTTCCAAAAGGTACAGTATGGAAAGGTGGGA AAGGAGTAACTTTACAGTGAAGAGACCTGACACGCACTACCTTAGCCAGGTGATCAA GGTCAACATC |
| 2 | CYP1A2 SNP rs2069514-G | CGAATTGTAACAAATATATTACACCACTGCAAGATGTTAATAATAGGGGAAACTGCAGA GTGGGGGTGGTAAATGGCCACTTTTACCTCCCTCATCATACTTTCCACTCAATTTTTCT GTGAACCAAAGACTGCTCTAAAAAAATCTATTAGCTTTTTAAAATTCCTTGGCTCCCCT CCAAAAAGTGTACATATGACATGATCTCATTTATGTAAAATACAACAAGCAAAACAAAT CCATGCAATAGATGTTGGGGTCATGGGTACCCTTGAGAAAGGAACACAACGGGACTT CTTGGATGCTTATGATGTCTCTTGATTAGAGCTGGTTATATGTGTGTTTGTTAAGTTTG CAAAAATTCATCAAGCTACACATGATCGAGCTATACATGACATATGCACTTTTCCATTT ATTTATTTATTTTTGAGACAGAATCTTGCTCTGTCACCCAGGCTGGAGTGCAGTGGTG CGATCTTGGCTCACCGCAACCTCCGCCTCTCGGATTCAAGCAATTGTCATGCCCCAG CTTCCCGAGTAGCTGGAATTACAGGTGTGCACCATCACGCCCAGCTAATTTTTTTTG TATTTTTAGTAGAGATGAGGTTTCACTATGTTGGCCAGGCTGGTCTTGAACTCCTGGC CTCACTCAAGTGATCCTCCCACCTCGGCCTCCCAAAGTGCTAGAATTACAGGTGTGA GTCACCGGTCCCAGCTGACATATGCACTTTTCTATATTGTATCCTGTAATTTAATTTTTT TAAGTTTTAAGAAAACATTAAAAATAAAAAGATAAATAGTCTGTCATACAGGAGAATTTC AAATAGTTTATGGAGATAATCCCCCCTCAAGGAGAAGGAGCGTAATCCCCCACTCCTT CGGTGTGGGCTGTGCATAGTGACTTCCTTCCAAAAGGTACAGTATGGAAAGGTGGGA AAGGAGTAACTTTACAGTGAAGAGACCTGACACGCACTACCTTAGCCAGGTGATCAA GGTCAACATC |
| 3 | CYP1A2 gene | GAAGCTCCACACCAGCCATTACAACCCTGCCAATCTCAAGCACCTGCCTCTACAGGTA CCTTTCTTGGGACCAATTTACAATCTCTGGGATCCCCAACTATAGAACCTGGAAGCTA GTGGGGACAGAAAGACGGGGAGCCTGGGCTAGGTGTAGGGGTCCTGAGTTCCGGG CTTTGCTACCCAGCTCTTGACTTCTGTTTCCCGATTTTAAATGAGCAGTTTGGACTAAG CCATTTTTAAGGAGAGCGATGGGGAGGGCTTCCCCCTTAGCACAAGGGCAGCCCTG GCCCTGGCTGAAGCCCAACCCCAACCTCCAAGACTGTGAGAGGATGGGGACTCATC CCTGGAGGAGGTGCCCCTCCTGGTATTGATAAAGAATGCCCTGGGGAGGGGCATC ACAGGCTATTTGAACCAGCCCTGGGACCTTGGCCACCTCAGTGTCACTGGGTAGGG GAACTCCTGGTCCCTTGGGTATATGGAAGGTATCAGCAGAAAGCCAGCACTGGCAGG GACTCTTTGGTACAATACCCAGCATGCATGCTGTGCCAGGGGCTGACAAGGGTGCTG TCCTTGGCTTCCCCATTTTGGAGTGGTCACTTGCCTCTACTCCAGCCCCAGAAGTGGA AACTGAGATGATGTGTGGAGGAGAGAGCCAGCGTTCATGTTGGGAATCTTGAGGCTC CTTTCCAGCTCTCAGATTCTGTGATGCTCAAAGGGTGAGCTCTGTGGGCCCAGGACG CATGGTAGATGGAGCTTAGTCTTTCTGGTATCCAGCTGGGAGCCAAGCACAGAACAC GCATCAGTGTTTATCAAATGACTGAGGAAATGAATGAATGTCTCCATCTCAACC CTCAGCCTGGTCCCTCCTTTTTTCCCTGCAGTTGGTACAGATGGCATTGTCCCAGTCT GTTCCCTTCTCGGCCACAGAGCTTCTCCTGGCCTCTGCCATCTTCTGCCTGGTATTCT GGGTGCTCAAGGGTTTGAGGCCTCGGGTCCCAAAGGCCTGAAAAGTCCACCAGAG CCATGGGGCTGGCCCTTGCTCGGGCATGTGCTGACCCTGGGGAAGAACCCGCACCT GGCACTGTCAAGGATGAGCCAGCGCTACGGGGACGTCCTGCAGATCCGCATTGGCT |

-continued

| SEQ ID NO. | SNP name | Sequence |
|---|---|---|
| | | CCACGCCCGTGCTGGTGCTGAGCCGCCTGGACACCATCCGGCAGGCCCTGGTGCG
GCAGGGCGACGATTTCAAGGGCCGGCCTGACCTCTACACCTCCACCCTCATCACTGA
TGGCCAGAGCTTGACCTTCAGCACAGACTCTGGACCGGTGTGGGCTGCCCGCCGGC
GCCTGGCCCAGAATGCCCTCAACACCTTCTCCATCGCCTCTGACCCAGCTTCCTCAT
CCTCCTGCTACCTGGAGGAGCATGTGAGCAAGGAGGCTAAGGCCCTGATCAGCAGG
TTGCAGGAGCTGATGGCAGGGCCTGGGCACTTCGACCCTTACAATCAGGTGGTGGT
GTCAGTGGCCAACGTCATTGGTGCCATGTGCTTCGGACAGCACTTCCCTGAGAGTAG
CGATGAGATGCTCAGCCTCGTGAAGAACACTCATGAGTTCGTGGAGACTGCCTCCTC
CGGGAACCCCCTGGACTTCTTCCCCATCCTTCGCTACCTGCCTAACCCTGCCCTGCA
GAGGTTCAAGGCCTTCAACCAGAGGTTCCTGTGGTTCCTGCAGAAAACAGTCCAGGA
GCACTATCAGGACTTTGACAAGGTGAGCCCGGGGTGCAGGTGGCAAGGGCACCTT
GCAGGGCCTGGGTGCAGCCCCTCCCTCCCAGCTCCAGCATGCCCACACAGCTGCTG
TGTTGCCAAGGCCTAGGAAGGCTCTGGACACCTCAGACCAGCTGTGTGACCTGGAGC
CGACTCTTCCCCTTCTCTGGGCCTCAGTTTCCTCATCCTTGAAGCCCCCTTCTCAGGG
CTCCTCAAAGCCCCCAAGAAAAAGCCCTGGAAATGGGGCCCTAGCAGAGTCCTGCA
ATGTGGGGGCCTATGAGTGAGAAAGCTTTCATTCTGCAGAAACCTAAACCCCAACA
GAGGCTAATCCCCAGCTCTGGTGTCACGTTGCTTCCCTGTGTTCACACTAACCTTTTC
CTTCTTTGAAATTGGACCCCTGGTGTTATTGGGAGGAAGGGTCAATGGGCATAAAAT
GACACTTTAAGCCATACCCAGGGCTGCTACCAGCTCCTGCTGCAAGCTGCAACCCCC
TGCCTAGAGACCAAGTTGGGAGGATAGGGGGGTACCCAGCCACCAGGTACAGGCCA
GGGGAGTGGAGCAACGTTCAGCCTTTGACCTTGGAAGTGCAGAGGTGCCCCTAAG
CTTGTGCCCCCTCAGAACAGTGTCCGGGACATCACGGGTGCCCTGTTCAAGCACAGC
AAGAAGGGGCCTAGAGCCAGCGGCAACCTCATCCCACAGGAGAAGATTGTCAACCTT
GTCAATGACATCTTTGGAGCAGGTAGGAACCAGAACCTTGCCCCTCCATCCAACAATG
CCTGCTGTTCACCCACAGCCTTGCCCAGCCCCTCAGTCCATGAAATAACCCACCAAC
CCTACACCAGATGGTACAACATACTGAGATCTGGCTTGGGATCAGGGTTTGAGCCTG
GGCTATGCCACCAATTCCCAGTGGAGAAACAGCAAAGTCCTTCTCCTCCCCTAGGCTT
CAGTTTCCCCATCTGAACAATAAGGTGTTCTCTGGCCTGTAAGTCTAGGCCCCTATAA
TTCCAGCAGCTAATTCTGAAACCTGTATCTCAAGTTTATGTTGAAGAGACCCAGCCTCT
GTCTTCAGGAAACTCACAGGCTAGGGCCAGAGAAAGCTAATGCTGGATACATACATA
GCAGATACTTGGGAAATGATGGTTTCCTTGTTTCTGTCTTCCTTCTTTCCTCACCTTAC
ACTACACGGTTCAGGATTTGACACAGTCACCACAGCCATCTCCTGGAGCCTCATGTAC
CTTGTGACCAAGCCTGAGATACAGAGGAAGATCCAGAAGGAGCTGGGTACATGGGG
GCCCCCAACCCTATAGCCAGGAGAAGCCTTGAGACCCAGGTTGTTTGTTCAGTCTAC
AAACACCTGTTATGTGCCTGCTGTGTGCAAGCCCTGGGCACACAGTAGTGCCTGCCC
TTGCCTAGAAGATGTGGGAGGTTAGTGGGGTCGCAGACTTGTGAATAGACAGTCTTA
CATAAGAGTGACATGGGGTATAAGAGGGGATAATTCATGGGGCAGTTAGGGCAGCCC
CTGAGCTCTGCTTGTCCTCTGTGTTCTACAGACACTGTGATTGGCAGGGAGCGGCGG
CCCCGGCTCTCTGACAGACCCCAGCTGCCCTACTTGGAGGCCTTCATCCTGGAGACC
TTCCGACACTCCTCCTTCTTGCCCTTCACCATCCCCCACAGGTGAGGCCTGCCGGTT
CTGCCCTCCCACCTCTAAAGTGCTTGCCATGTTTTCTCTTCCTGGCTTCTCAGCCCTG
GCCCTGGCTCAGCATCTCCTTCCCGACCTCGTTCCCCACAGATCCCGGCCTCAGTCT
GCCCCCATCCAGTCCAAACATAATCTAACCCCCAGCTCTCAGGAGAAAGTTCCACTTG
TGATCTCAGCGCTCATTCCCCTCTGTTCATATTCCCTCCCTCCCAGTGCCCTCTGTGC
CAGTCAGGTCGGCCTCACCCTCACAAGCATGACCCTATTGGCCTCCAATCTTGCTAAC
GCTGAACCTTCTGCCTGGAATACCTTCTAGCCTCTTCTCTGACCACCAGAATCCTACC
CTTGCTCAAAGTCAATGCCGACACGAGCTTCCTCTCCCCAGAAGCCTTTTGACTCATC
CAGCTGGCACAGCTTCATTCCTGATGTCTTATAGGACTTACAGCCATCAGCCCTTGAT
CATGCCCTGGAATTTTAACAATGTCAAGAGAGTTAGTGAGCATTTACTTCTACCCAAAC
GTTGTTCTAGTTATTCCTGCAGTAAGAGGCCTGAATCCCCAGCCAGGCTAGAAATTCC
CCGGGGCTGCCCCAGGCTGCCTGCTGCTTTTTTTTTTTTTTTTTTTTTCATAGAAA
ATAGAAAAACATTTATCTGAAATTGCCTGCTTCTTGGCTCCAGAGAACAGCCAAGTGC
GCAGCCAGGCGCAAAGAGAAGTTTAGTAAATACTTGCTGAAGTTAAAGAACAGGACG
CAAGGAAGAGGGAGGATGTTTCTACCTCTTCCCTGTTCCTCCCTCCCCTCCCAGTGT
AGGGATGGAGATGGCGGTGGGCAGGCTGTCTGGATGGGGTGGAGGTAGGAGCAAC
ACATGCCCCAGCTTTCCAGCCCTGAGCCTCACAGTGCCCTCTTCCCTCCTCAGCACA
ACAAGGGACACAACGCTGAATGGCTTCTACATCCCCAAGAAATGCTGTGTCTTCGTAA
ACCAGTGGCAGGTCAACCATGACCCGTGAGTACATACCCCTCACGAAAAAATGTGTG
CAGGTTCAGCAGTCAGGAAGGCTGTTTGTCCCTGCTAGGAACTGTTTATATAATGAAA
GGAGGGGACCTCAATTGCTATAGTCTGCTCTAAGTGACGATATTTACAAAAGTTTCAC
AAACTTTAGTGCACAGGAATCAACTAGGATGGCCAGGCGCAGTGGCTCAAGCCTATA
ATCCCAGCAGTTTGGGAGGCCGAGGCAGGCAGATCACTTGAGGTCAGGAGTTTGAG
ACCAGCCTGGGCAACATGGTGAAACCCTATCTCTACTAAAAATACAAACAAAAATTA
GCCGGACATGGTGGTGCGCCTATAATCCCAGCTACTCCAGAGGCTGAGGCAGGAGA
ATTGCTTGAACTCTGGAGGTAGAGGCTGCAGTGAGCCGAGATCGCTCCACTGCACTC
CAGCCTGGGTGACGGAGTGAGACTCTGCCTCAAAAAAAAAAAAAAAAAATCAACCAAG
ACGTTTGTTACAGGTGATGGTTCCCCAGGATTCTACTGTGGTATCTAAGGTGGGGTA
CCTCAGGCGATTCTGATGTGAATGGCTCAGAGACCTCTCTTTGGAAAGCCCCACTTTA
GTGTATAGGTAGGGGACCATATATATAATTTACCATCCACACTGGGACATTTGAGTG
TGAAAATGCTATCAATGTTTATGCTAGTCATCATTACTCCAAAACAATAAACATAAGCC
AGGACATACTGTTGAGGCCCCTTAGGAGGCATATTTTGAGTAGGATGAAGAAACGTAT
GTCTTTCTTTCTTCCTTTCACTTTAATTTTTAAATAGAGACAAGGTCTTCCTATGTGGTC
CAGGCTGGTTTTGAACTCCTGGTTCAAGGGATCTTCCTGCCTCAGCCTCCCAAAGT
GCTAGGGTTACGGGTGTAAGCCACCAAACCCAGCCTGTTTTTCTTCTTTTAATTTCTTT |

-continued

| SEQ ID NO. | SNP name | Sequence |
|---|---|---|
| | | TAGATAAAGCATTATTTAAAGTAAATTAATATTAAAAGGCACTATCTTTAAGGCTGGTCA<br>TTTTAGAGAGAGCTTTGTAAAAGAAATAAGCATCAGGCCAGGTGTGGTGACTCATGCC<br>TGTAACCCCAGCACTTTGGGAGTCCGAGGAAGGTGGATCGCTTGAGCTCATGAGTCT<br>GAGACCAGTGAAACCCCGTCTCTGCAAAAAAAAAAAAAAAAAAAAATACAAAAATTAG<br>CCGGATATGGTGCCTGTAGTCCCAGCTACACGGGAGGCTCAGGTGGGTGGTTGGCT<br>TGAGCTGGGGAGGCAGAGAGAGTGCAGTGAGCTGAGATCGCACCACTGTACTCCAG<br>CCTGGGTGATAGGAGCCGGAGGGTGTCTCAAAAAAAAAAAAAGAAAGAAAAGAAAAA<br>GAAATAAGCATCAAAGTTCAGTTTGGTTCCTTCCCACCTACCCTTCATTGCTTTCAAAG<br>TGCCCTCACACTTGTGTTCTCAACAGAAGTCTCCCTCCCCCAGGCACCTCCTCCCAG<br>GGCCTCTCCAGCCCTGAGGTCCCATCTCCTCTGTTCCTCTTGCAGAGAGCTGTGGGA<br>GGACCCCTCTGAGTTCCGGCCTGAGCGGTTCCTCACCGCCGATGGCACTGCCATTAA<br>CAAGCCCTTGAGTGAGAAGATGATGCTGTTTGGCATGGGCAAGCGCCGGTGTATCGG<br>GGAAGTCCTGGCCAAGTGGGAGATCTTCCTCTTCCTGGCCATCCTGCTACAGCAACT<br>GGAGTTCAGCGTGCCGCCGGGCGTGAAAGTCGACCTGACCCCCATCTACGGGCTGA<br>CCATGAAGCACGCCCGCTGTGAACATGTCCAGGCGCGGCTGCGCTTCTCCATCAACT<br>GAAGAAGACACCACCATTCTGAGGCCAGGGAGCGAGTGGGGGCCAGCCACGGGGA<br>CTCAGCCCTTGTTTCTCTTCCTTTCTTTTTTTAAAAAATAGCAGCTTTAGCCAAGTGCA<br>GGGCCTGTAATCCCAGCATTTTAGGAGGCCAAGGTTGGAGGATCATTTGAGCCCAGG<br>AATTGGAAAGCAGCCTGGCCAACATAGTGGGACCCTGTCTCTACAAAAAAAAAATTTG<br>CCAAGAGCCTGAGTGACAGAGCAAGACCCCATCTCAAAAAAAAAAACAAACAAACAAA<br>AAAAAAACCATATATATACATATATATATAGCAGCTTTATGGAGATATAATTCTTATGCC<br>ATATAATTCACCTTCTTTTTTTTTTTTGTCTGAGACAGAATCTCAGTCTGTCACCCAGG<br>TTGGAGTGCAGTGGCGTGATCTCAGCTCACTGCAACCTCCACCTCGCAGGTTCAAGC<br>AATCCTCCCACTTCAGCCTCCCAAGCACCTGGGATTACAAGCATGAGTCACTACGCCT<br>GGCTGATTTTTGTAGTTTTAGTGGAGATGGGGTTTCACCATGTTGGCCAGGCTTGTCT<br>CGAACTCCTGACCCCAAGTTATCCACCTGCCTTGGCTTCCCAAAGTCCTGGGATTACA<br>GGTGTGAGCCACCACATCCAGCCTAACTTACATTCTTAAAGTGTCGAATGACTTCTAG<br>TGTAGAATTGTGCAACCATCACCAGAATTAATTTTATTATTCTTATTATTTTTGAGACAG<br>AGTCTTACTCTGTTGCCAGGCTGGAGTGCAGTGGCGCGATCTCAGCTCACTACAACC<br>TCCGCCTCCCATGTTCAAGCGATTCTCCTGCCTCAGCCTCCCGAGTAGCTGGGACTA<br>TAGGCATGCGCCACCATGGCCAGCTAATTTTTGTATTTTTAGTAGAGACGAGGTTTCA<br>CTGTGTTGGCCAGGATGGTCTCCATCTCTTGACCTCGTGATCCACCCGCCTCAGCCT<br>CCCAAAGTGCTGGGATTAACAGGTATGAACCACCGCGCCCAGCCTTTTTGTTTTTTTT<br>TTTTTTGAGACAGAGTCTTCCTCTGTCTCCTAAGCTGGAGTGCAGTGGCATCATCTCA<br>GCTCACTGCAACCTCTGCCTCCCAGGTTCAAGTGCTTCTCCAGCCTCAGCCTCCCAA<br>GTAGCTGAGACTACAGGCACACACCACCACGCCTGGCTAATTTTTGTATTTTTAGTAG<br>AGACGGGTTTCACCATGTTGGCTAGACTAGTCTCAAACTCCTGACCTCAAGTGATCTG<br>CCCGCCTCGACCTCTCTCAAAGTGCTGGCATTACAGGTGTGAGCCACGGTGCCCGG<br>CCCACAATTAATTTTAGAACATTTTCATCACCCCTAAAAGAAACCCTGCACCCATTAGC<br>AGTCCCTCCACATTTCCCCCTAGCCTGCCTCCCCTGCCTCACCAGCCCTGGCAACTG<br>CTAATCTACTTTCTGTGTCTATGGATTTGCCTTCTCTAAACATTTCATATAAATGGAATT<br>ACACAATG |

EXAMPLES

General Methodology

To measure the effect of alpha 7 nicotinic acetylcholine receptor activator treatment on the cognitive skills of schizophrenic patients, an adequate cognitive test battery (CogState™) with short duration (as described in detail below) was applied allowing multiple time points measurements during the treatment period (Pietrzak, et al 2009; Maruff, et al 2009).

Continuous Paired Associates Learning (CPAL) Test

The CPAL task is a validated test that assesses visual episodic memory (associate learning). This test has been used previously in schizophrenia. Before beginning this task, the test supervisor reads the full instructions to the patient from the test supervisor script. On the CPAL test, participants must learn a series of associations between a set of difficult to verbalize patterns and locations. In the presentation phase of the task, the pattern appears at the location and the subject is required to acknowledge that they have seen the pattern by touching the location at which it appears. At this stage of the task the patient will also see that there are two locations at which no target appears (distractor locations). Patterns are presented, in random order. However, once presented the pattern remains at the same location throughout the task. In the learning phase of the task, patients must place each of the eight patterns in their correct locations. They must do this in six rounds. For the first round, one of the patterns is presented in the centre location and the subject is required to remember the location at which it had been shown. They indicate the location by touching it. If they touch the incorrect location, a visual and audible signal occurs (a red cross appears over the location and a buzzer sound is presented). The patient is then required to choose a second location. This process continues until the patient has correctly placed all four of the targets in their correct locations. Once all eight patterns have been placed correctly, the second round begins. In the second round the patterns remain in the same locations, but their order of presentation in the centre of the screen is different to that of the first round (randomized). The process of placing each target in the correct location proceeds as it did in the first round. When the second round is complete, the same process is repeated as the rounds progress the number of errors made in placing the patterns in their correct locations reduces. Administration time is approximately 5 minutes in healthy volunteers. Patients with Schizophrenia would be expected to complete the task within about 12 minutes.

Statistical Methods for Pharmacodynamics Analyses

The assessment of activity was obtained from a statistical analysis of the post dose Area Under the Effect Curve (AUEC) 4-10 on CPAL as follows: variables were separately analyzed by means of a linear mixed effect model adjusted for the period-specific baseline value for the scale, the treatment group, the period, and the sequence as fixed effects, and for the patient as a random effect. The period-specific baseline value for the scale was obtained from the average of the period-specific Day −1 values and from the pre-dose value. The mean treatment difference (and its 95% CI) between each B-5 dose group and placebo was obtained from the model. The effect size was obtained by dividing the mean treatment difference (and its 95% CI) by the square root of twice the estimated variance of the residual error. Activity, as defined in the paragraph above, was assessed from the effect size of CPAL.

Example 1

Study Set Up to Identify if a Subset of Patients Exist that Respond to B-5 Treatment In an attempt to identify a subset of patients who respond to B-5 treatment, a study in a population of 29 individuals using the CPAL assessment was conducted. The purpose was to investigate the relationship between the genetic variants rs2069514 (SEQ IDs NO. 1 and 2) in the CYP1A2 gene and B-5 efficacy in the study. In the study, B-5 mono-fumarate was used in the form of hard gelatin capsules as described in Example E.

Clinical Samples: Genomic DNA from 29 individuals was extracted from whole blood according to the instructions from Gentra Systems, Inc. (Minneapolis, Minn.).

Genotyping Assay: A total of 29 DNA samples were genotyped for rs2069514 (SEQ IDs NO. 1 and 2) in the CYP1A2 gene. Genotyping was performed using TaqMan Assays-by-Design and Assays-on-Demand (Applied Biosystems, Foster City, Calif.) on an ABI 7900 sequencer. Genotyping used 1 ng of genomic DNA according to manufacturer's instruction.

Statistical Analysis: A mixed effect model including sequence, period and treatment as fixed effects, baseline value as covariate and subject as random effect was used. The effect size was determined by the difference in estimated means B-5-Placebo Treatment divided by the square root of twice the estimated variance of the residual error. Baseline disease severity was analyzed by ANCOVA (analysis of covariance) adjusted for age, gender, years of education, and smoking history.

Results: The patients who were homozygous or heterozygous for the "A" variant (SEQ ID NO. 1) of the CYP1A2 SNP rs2069514-(A/A or A/G) showed significant response to B-5 on "visual learning and memory" (CPAL) compared to placebo (2 mg: p=0.018, 15 mg: p=0.0023, and 100 mg: p=0.0043), as can be seen in Table 1. The effect size in the three treatment arms was 0.68, 0.91 and 0.83, respectively. In contrast, the patients who were homozygous for the "G" variant (SEQ ID NO: 2) of the CYP1A2 SNP rs2069514-G/G did not show any significant improvement on cognitive function, as can be seen in Table 2. The results showed that the "AA" and "AG" genotypes of the CYP1A2 SNP rs2069514 is a predictive marker of clinical response to B-5 in patients with schizophrenia. Another way to state this is that the "GG" genotype of the CYP1A2 SNP rs2069514-G (SEQ ID NO. 2) is a negative predictive marker of clinical response to B-5 in patients with schizophrenia.

TABLE 1

Primary clinical endpoint CPAL assessment of CogState ™ test battery by CYP1A2 genotypes AA + AG (n = 14)

| CogState domain | Treatment | Estimated mean AUC 4-10 | Effect size | Placebo - B-5 (95% CI) | P-value* |
|---|---|---|---|---|---|
| CPAL-AUC4-10 (Total # errors × Hours) | Overall | | | | 0.0089 |
| | Placebo | 523.03 | | | |
| | B-5 2 mg | 411.15 | 0.68 | (0.124, 1.226) | 0.018 |
| | B-5 15 mg | 372.82 | 0.91 | (0.352, 1.462) | 0.0023 |
| | B-5 100 mg | 384.9 | 0.83 | (0.283, 1.385) | 0.0043 |

TABLE 2

Primary clinical endpoint CPAL assessment of CogState ™ test battery by CYP1A2 genotype GG (n = 15)

| CogState domain | Treatment | Estimated mean AUC 4-10 | Effect size | Placebo - B-5 (95% CI) | P-value* |
|---|---|---|---|---|---|
| CPAL-AUC4-10 (Total # errors × Hours) | Overall | | | | 0.8048 |
| | Placebo | 451.79 | | | |
| | B-5 2 mg | 414.75 | 0.15 | (−0.407, 0.708) | 0.59 |
| | B-5 15 mg | 481.4 | −0.12 | (−0.685, 0.445) | 0.6706 |
| | B-5 100 mg | 457.45 | −0.02 | (−0.582, 0.536) | 0.9344 |

Example A

Preparation of 5-chloro-2-(4-methylphenyl)pyridine

Under nitrogen 2,5-dichloro-pyridine (40 g, 270 mmol), 4-methylphenylboronic acid (39 g, 289 mmol) and bistriphenylphosphin-palladium(II) dichloride (1.14 g; 1.6 mmol) were suspended in water (258 g)/THF (117 g) for approx. 30 min at 35-55° C. A solution of tripotassium phosphate (143.4 g, 676 mmol) in water (143 g) was added at 35-55° C. during approx. 60-120 min and 55° C. was maintained for another approx. 30-45 min. More tripotassium phosphate (22.9 g, 108 mmol) in water (22.9 g) was added over a period of approx. 30 min and the temperature was raised to 55-60° C. to complete the reaction within another approx. 2h.

For extractive palladium removal a solution of cysteine (ca. 16 g) in water (115 g) was added to the reaction mixture at 60-55° C. After approx. 1h at 55° C. the biphasic reaction mixture was clarified by filtration over a pad of cellflock filter aid (2-5 g) and a THF/water mixture (110 g/75 g) was used for rinsing. The layers of the combined filtrates were separated at 25° C. and the salt containing water layer was extracted with THF (1×57 g). The combined THF layers were diluted with ethanol 94% (195 g) and concentrated by distillation under reduced pressure (300-200 mbar) at a jacket temperature of 45° C. in order to remove the bulk of THF (175-250 g). To the remaining product solution further ethanol (97 g) was added and at 45-55° C. water (565 g) was gradually added over a period of approx. 60 min to induce and maintain crystallization. After 30 min the temperature was lowered to approx. 20° C. in approx. 90-120 min and after another hour at that temperature the solids were collected by filtration, washed with ethanol/water 1:2 and dried under reduced pressure to yield 5-chloro-2-(4-methylphenyl)pyridine (52.5 g; 95% of theory; purity >95%; Pd <25 ppm).

Example B

Preparation of (R)-3-(6-(4-methylphenyl)-pyridin-3-yloxy)-1-aza-bicyclo[2.2.2]octane in free form and fumarate salt form Example B1

Formation of Free Form

Under nitrogen, to 3R-quinuclidinol (43.8 g, 0.34 mol) in DMSO (792 g) an approx. 20% THF solution of potassium tert-butoxide (210 g, 0.375 mol) was added and at approx. 40-45° C. under reduced pressure the THF solvent was distilled off. The temperature of the reaction mixture was raised to 90° C. and the solid 5-chloro-2-(4-methylphenyl) pyridine (61.2 g, 0.30 mol) was gradually added in at least 4 portions. The temperature was raised further to approx. 100-105° C. and after at least another 3 hours at this temperature the reaction to (R)-3-(6-(4-methylphenyl)-pyridin-3-yloxy)-1-aza-bicyclo[2.2.2]octane was complete.

Water (150 g) was added to the reaction mixture at 60-25° C. and the temperature was gradually lowered to approx. 20° C. in approx. 60 min and additional water (210 g) was added. After at least another 2 further hours at this temperature the fine solids were collected by filtration, washed successively with DMSO/water (approx. 322 g; 2:1 mixture), water (500 g) and water/ethanol (approx. 500 g; 9:1 mixture) and dried at 60° C. under reduced pressure to yield (R)-3-(6-(4-methylphenyl)-pyridin-3-yloxy)-1-aza-bicyclo[2.2.2]octane (56.3 g, 63% of theory).

Example B2

Formation of Fumarate Salt Form

To a clear solution of (R)-3-(6-(4-methylphenyl)-pyridin-3-yloxy)-1-aza-bicyclo[2.2.2]octane (39.6 g; 0.135 mol) and fumaric acid (16.4 g, 0.141 mol) in ethanol (330 g)/water (21 g) at 65° C. tert.-butylmethylether (142.5 g) was added and the reaction mixture was cooled to 23° C. in approx. 60 min. Further tert.-butylmethylether (170.6 g) was added. After at least another 2 hours the solids were collected by filtration, washed with ethanol/tert.butylmethylether (153 g; 1.1 mixture) and dried at 55-60° C. under reduced pressure to yield (R)-3-(6-(4-methylphenyl)-pyridin-3-yloxy)-1-aza-bicyclo [2.2.2]octane hydrogenfumarate (43.8 g, 79% of theory).

Example C

Preparation of (R)-3-(6-(4-methylphenyl)-pyridin-3-yloxy)-1-aza-bicyclo[2.2.2]octane in free form and fumarate salt form Example C1

Formation of Free Form

Under nitrogen to 3R-quinuclidinol (41.4 g, 0.325 mol) in DMSO (320 g) a solution of 5-chloro-2-(4-methylphenyl) pyridine (51 g, 0.250 mol) in toluene (201 g) was added. The temperature was raised gradually to approx. 100-105° C. while residual water, if any, was removed by refluxing under reduced pressure at a water trap for ca. 45 min. Over a period of approx. 90 min an approx. 20% THF solution of potassium tert-butoxide (158.8 g, 0.283 mol) was continuously added while gradually the THF solvent distills off. After another 2-5 hours at approx. 100-105° C. the reaction to (R)-3-(6-(4-methylphenyl)-pyridin-3-yloxy)-1-aza-bicyclo [2.2.2]octane was complete.

Water (293 g) was added to the reaction mixture at 60-25° C. The layers were separated and the toluene layer was washed with water (2×42 g). The toluene solution was dried at ca. 60° C. by refluxing under reduced pressure at a water trap for ca. 45-60 min.

Example C2

Formation of Fumarate Salt Form

To the toluene solution of Example C1, at ca. 50-55° C., a slurry of fumaric acid (26.1 g, 0.9 eq) in EtOH 94% (22 g) and toluene (97 g) was gradually added. Further toluene (97 g) was added for rinsing and after another ca. 30-60 min at 55° C. the temperature was gradually lowered to approx. 20° C. in approx. 120-180 min. After at least another 1 hour the solids were collected by filtration, washed with water saturated toluene (2×104 g) and dried at 60° C. under reduced pressure to yield (R)-3-(6-(4-methylphenyl)-pyridin-3-yloxy)-1-aza-bicyclo[2.2.2]octane hydrogenfumarate (84.8 g; 82% of theory, based on amount of 5-chloro-2-(4-methylphenyl)pyridine used in Example C1).

Example D

Preparation of mono-fumarate salt of (R)-3-(6-(4-methylphenyl)-pyridin-3-yloxy)-1-aza-bicyclo[2.2.2] octane in crystalline form 500 mg of (R)-3-(6-(4-methylphenyl)-pyridin-3-yloxy)-1-aza-bicyclo[2.2.2]octane in free base form were suspended in 20 ml isopropyl alcohol. A stochiometric amount of fumaric acid was added. The resulting solution was stirred at ambient temperature for 14 hours. The precipitate was collected by filtration.

Example D1

Preparation of mono-fumarate salt of (R)-3-(6-(4-methylphenyl)-pyridin-3-yloxy)-1-aza-bicyclo[2.2.2] octane in crystalline form by seeded crystallization 7.3 g mono-fumarate of (R)-3-(6-(4-methylphenyl)-pyridin-3-yloxy)-1-aza-bicyclo[2.2.2]octane (purity >98%; prepared as described e.g. in Example C2) was dissolved in ethanol (42.9 g)/isopropanol (8.5 g)/water (7.2 g) at about 50° C., clarified by filtration and added at this temperature gradually over a period of about 8 hours to filtered tertiary-butylmethylether (118.4 g) at a temperature of about 50° C. After about 25% of the filtrate was added, an ultrasonificated suspension of seed crystals of the mono-fumarate of (R)-3-(6-(4-methylphenyl)-pyridin-3-yloxy)-1-aza-bicyclo[2.2.2] octane (6 mg, prepared e.g. as described in Example C2) in isopropanol (0.1 ml) was added to induce crystallization. The product suspension was maintained for another 1 hour at 50° C. and cooled to 0° C. within 8 hours. After another 1 hour at this temperature the solids were isolated by filtration, washed with isopropanol/tertiary-butylmethylether (40 ml, 1:1 mixture) and dried at about 50° C. under reduced pressure to yield the mono-fumarate of (R)-3-(6-

(4-methylphenyl)-pyridin-3-yloxy)-1-aza-bicyclo[2.2.2]octane (5.85 g; 81% of theory; purity >99.5%).

Example E

Hard Capsules

Hard gelatin capsules, each comprising as active ingredient 0.5, 5 or 25 mg of the mono-fumarate of (R)-3-(6-(4-methylphenyl)-pyridin-3-yloxy)-1-aza-bicyclo[2.2.2]octane can be prepared as follows:

| Ingredient for capsule fill | % (w/w) for 0.5 mg capsules | % (w/w) for 5 mg capsules | % (w/w) for 25 mg capsules |
| --- | --- | --- | --- |
| Mono-fumarate of (R)-3-(6-(4-methylphenyl)-pyridin-3-yloxy)-1-aza-bicyclo[2.2.2]octane | 0.46 | 4.65 | 23.23 |
| Lactose monohydrate | 65.24 | 61.05 | 42.47 |
| Microcrystalline cellulose | 25.00 | 25.00 | 25.00 |
| Hypromellose | 2.50 | 2.50 | 2.50 |
| Sodium croscarmellose | 6.00 | 6.00 | 6.00 |
| Colloidal silicon dioxide | 0.30 | 0.30 | 0.30 |
| Magnesium stearate | 0.50 | 0.50 | 0.50 |
| Purified water* | q.s. | q.s. | q.s. |

*removed during processing

Preparation process: Mono-fumarate of (R)-3-(6-(4-methylphenyl)-pyridin-3-yloxy)-1-aza-bicyclo[2.2.2]octane, lactose monohydrate, microcrystalline cellulose, a portion of sodium croscarmellose and hypromellose were dry mixed in a high shear mixer bowl, and granulating fluid (purified water) added. Once the granulation was complete, the wet granules were dried in a fluid bed drier and the dry granules were milled. The remaining sodium croscarmellose and colloidal silicon dioxide were passed through a suitable sieve and added to the dried granular material and blended in a suitable blending shell. This was achieved by co-sieving the sodium croscarmellose and the colloidal silicon dioxide with a portion of the milled granules through a suitable sieve into the blending shell. Similarly, the required amount of sieved magnesium stearate was added to the bulk granule and then mixed in the same blending shell. This final blend was encapsulated into capsules using automated equipment. Weight ratio of capsule fill to empty capsule shells was 2:1.

Example F

Tablets

Example F1

Film-coated Tablet

Film-coated tablets containing e.g. 0.5 mg of the mono-fumarate of (R)-3-(6-(4-methylphenyl)-pyridin-3-yloxy)-1-aza-bicyclo[2.2.2]octane may be prepared as follows:
Preparation of Pre-mix:
Weigh-in mono-fumarate of (R)-3-(6-(4-methylphenyl)-pyridin-3-yloxy)-1-aza-bicyclo[2.2.2]octane (e.g. approx. 0.7%) and maize starch (e.g. approx. 13%), mix in a tumble blender (approx 100-300 rotations), pass through a sieve of approx. 0.25-1.0 mm mesh-size. Mix in a tumble blender (approx. 100-300 rotations).
Preparation of Final Blend:
To above pre-mix add microcrystalline cellulose (e.g. approx. 25%), sprayed lactose (e.g. approx. 68%), sodium-carboxymethylcellulose XL (e.g. approx. 2%) and Aerosil (e.g. approx. 0.5%) and mix in a tumble blender (approx. 100-300 rotations). Pass this mixture through a sieve of approx. 0.5-1.0 mm mesh-size and mix again (approx. 100-300 rotations).
Add the sodium-stearyl-fumarate (e.g. approx. 1.5%) through a handsieve at approx. 0.5-1.0 mm mesh-size and mix in a tumble blender (approx. 30-150 rotations).
Compression:
On a rotary press compress the above final blend to cores of approx. 100 mg, using the dosage specific tooling (e.g. approx. 6 mm, round, curved).
Coating:
Prepare a suspension in water with basic coating premixes black, red, yellow and/or white. Coat the above obtained cores in a perforated coating pan, and dry.

Example F2

Bilayer Film-coated Tablet

Bilayer film-coated tablets containing e.g. 2.5 mg of the mono-fumarate of (R)-3-(6-(4-methylphenyl)-pyridin-3-yloxy)-1-aza-bicyclo[2.2.2]octane may be prepared as follows:
Final Active Blend:
Weigh-in mono-fumarate of (R)-3-(6-(4-methylphenyl)-pyridin-3-yloxy)-1-aza-bicyclo[2.2.2]octane coarse (e.g. approx. 15.5%), microcrystalline cellulose (e.g. approx. 25%), sprayed lactose (e.g. approx. 53%), sodium-carboxymethylcellulose XL (e.g. approx. 3%) and Aerosil (e.g. approx. 0.5%) and mix in a tumble blender (approx 100-300 rotations). Pass this mixture through a sieve of approx. 0.5-1.0 mm mesh-size and mix again (approx 100-300 rotations).
Add the Na-stearyl-fumarate (e.g. approx. 3%) through a handsieve at approx. 0.5-10 mm and mix in a tumble blender (approx 30-150 rotations).
Final Placebo Blend:
Weigh-in microcrystalline cellulose (e.g. approx. 26%), sprayed lactose (e.g. approx. 69%), sodium-carboxymethylcellulose XL (e.g. approx. 1.9%) and Aerosil (e.g. approx. 0.5%) and mix in a tumble blender (approx 100-300 rotations). Pass this mixture through a sieve of approx. 0.5-1.0 mm mesh-size and mix again (approx 100-300 rotations). Add the sodium-stearyl-fumarate (e.g. approx. 3%) through a handsieve at approx. 0.5-1.0 mm and mix in a tumble blender (approx 30-150 rotations).
Compression:
On a rotary press compress the above final blends to a bilayer tablet-core of approx. 100 mg with one placebo layer (approx. 77.5 mg) and one active layer (approx. 22.5 mg), using the dosage specific tooling (e.g. approx. 6 mm, round, curved).
Coating:
Prepare a suspension in water with basic coating premixes black, red, yellow and/or white. Coat the above obtained cores in a perforated coating pan, and dry.

Example F3

Film-coated Tablet

Film-coated tablets containing e.g. 50 mg of the mono-fumarate of (R)-3-(6-(4-methylphenyl)-pyridin-3-yloxy)-1-aza-bicyclo[2.2.2]octane may be prepared as follows:

Final Blend:

Weigh-in mono-fumarate of (R)-3-(6-(4-methylphenyl)-pyridin-3-yloxy)-1-aza-bicyclo[2.2.2]octane coarse (e.g. approx. 15.5%), microcrystalline cellulose (e.g. approx. 25%), sprayed lactose (e.g. approx. 53%), sodium-carboxymethylcellulose XL (e.g. approx. 3%) and Aerosil (e.g. approx. 0.5%) and mix in a tumble blender (approx. 100-300 rotations). Pass this mixture through a sieve of approx. 0.5-1.0 mm mesh-size and mix again (approx. 100-300 rotations).

Add the sodium-stearyl-fumarate (e.g. approx. 3%) through a handsieve at approx. 0.5-10 mm and mix in a tumble blender (approx. 30-150 rotations).

Compression:

Compress the above final blend on a rotary press to cores, using the dosage specific tooling (e.g. approx. 15*5.9 mm, round, curved).

Coating:

Prepare a suspension in water with basic coating premixes black, red, yellow and/or white. Coat the above obtained cores in a perforated coating pan, and dry.

REFERENCES

1. Chini B, Raimond E, Elgoyhen A B, Moralli D, Balzaretti M, Heinemann S (1994). —Molecular cloning and chromosomal localization of the human alpha 7-nicotinic receptor subunit gene (CHRNA7). Genomics 19: 379-381.
2. Freedman R, Hall M, Adler L E, Leonard S (1995).— Evidence in postmortem brain tissue for decreased numbers of hippocampal nicotinic receptors in schizophrenia. Biological. Psychiatry 38: 22-33.
3. Freedman R, Coon H, Myles-Worsley M, Orr-Urtreger A, Olincy A, Davis A, Polymeropoulos M, Holik J, Hopkins J, Hoff M, Rosenthal J, Waldo M C, Reimherr F, Wender P, Yaw J, Young D A, Breese C R, Adams C, Patterson D, Adler L E, Kruglyak L, Leonard S, Byerley W (1997).— Linkage of a neurophysiological deficit in schizophrenia to a chromosome 15 locus.—Proceedingsof the National Academy of Sciences of the United States of America. 94: 587-592.
4. Goldberg T E, Goldman R S, Burdick K E, Malhotra A K, Lencz T, Patel R C, Woerner M G, Schooler N R, Kane J M, Robinson D G (2007).—Cognitive improvement after treatment with second-generation antipsychotic medications in first-episode schizophrenia: is it a practice effect?—Archives of General Psychiatry 64: 1115-1122.
5. Green M F (1996).—What are the functional consequences of neurocognitive deficits in schizophrenia?. American Journal of Psychiatry 153: 321-330.
6. Green M F (2007).—Cognition, drug treatment, and functional outcome in schizophrenia: a tale of two transitions. American Journal of Psychiatry 164: 992-994.
7. Harvey P D, Green M F, Keefe R S, Velligan D I (2004).—Cognitive functioning in schizophrenia: a consensus statement on its role in the definition and evaluation of effective treatments for the illness. Journal of Clinical Psychiatry 65: 361-372.
8. Keefe R S, Bilder R M, Davis S M, Harvey P D, Palmer B W, Gold J M, Meltzer H Y, Green M F, Capuano G, Stroup T S, McEvoy J P, Swartz M S, Rosenheck R A, Perkins D O, Davis C E, Hsiao J K, Lieberman J A, CATIE I,—Neurocognitive Working Group (2007). —Neurocognitive effects of antipsychotic medications in patients with chronic schizophrenia in the CATIE Trial.— Archives of General Psychiatry 64: 633-647.
9. Leonard S, Gault J, Hopkins J, Logel J, Vianzon R, Short M, Drebing C, Berger R, Venn D, Sirota P, Zerbe G, Olincy A, Ross R G, Adler L E, Freedman R (2002). —Association of promoter variants in the alpha7 nicotinic acetylcholine receptor subunit gene with an inhibitory deficit found in schizophrenia. Archives of General Psychiatry 59: 1085-1096.

The invention claimed is:

1. A therapeutic method of increasing the cognitive skills of an individual and/or treating a cognitive impairment, psychotic and/or neurodegenerative disorder, the therapeutic method comprising:

administering a therapeutically effective amount of an alpha 7 nicotinic acetylcholine receptor activator to the individual, wherein the individual has been selected according to a method comprising the steps of:

obtaining the genotype of the individual at the genetic locus of the human cytochrome P450, family 1, subfamily A, polypeptide 2 (CYP1A2) gene; and determining that the individual's CYP1A2 genotype includes (i) a homozygous SNP genotype of rs2069514-A/A, or (ii) a heterozygous SNP genotype of rs2069514-A/G, or (iii) a SNP forming a haplotype with said SNP genotypes or a SNP in the same linkage disequilibrium with said SNP genotypes.

2. The therapeutic method of claim 1, wherein the alpha 7 nicotinic acetylcholine receptor activator is a compound of formula (I)

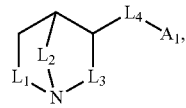

wherein $L_1$ is —$CH_2$—; $L_2$ is —$CH_2$— or —$CH_2$—$CH_2$—; and $L_3$ is —$CH_2$— or —$CH(CH_3)$—; or $L_1$ is —$CH_2$—$CH_2$—; $L_2$ is —$CH_2$—; and $L_3$ is —$CH_2$—$CH_2$—;

$L_4$ is a group selected from

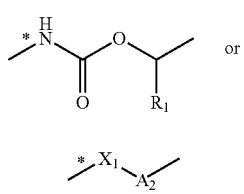

wherein the bond marked with the asterisk is attached to the azabicycloalkyl moiety;

$R_1$ is hydrogen or $C_{1-4}$alkyl;

$X_1$ is —O— or —NH—;

$A_2$ is selected from

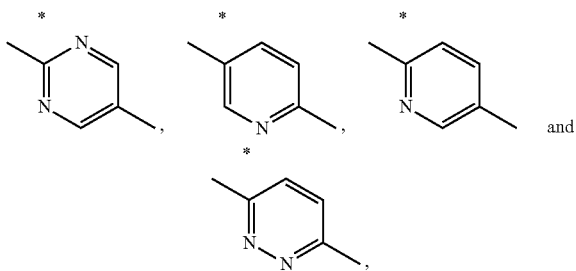

wherein the bond marked with the asterisk is attached to $X_1$;

$A_1$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_2$, and wherein a substituent on a nitrogen in a heterocyclic ring system may not be halogen;

each $R_2$ independently is $C_{1-6}$alkyl, $C_{1-6}$halogenalkyl, $C_{1-6}$alkoxy, $C_{1-6}$halogenalkoxy, halogen, cyano or a three- to six-membered monocyclic ring system which may be aromatic, saturated or partially saturated and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;

or two $R_2$ at adjacent ring atoms form a $C_{3-4}$alkylene group, wherein 1-2 carbon atoms may be replaced by $X_2$, and wherein the $C_{3-4}$ alkylene group may be substituted once or more than once by $R_3$;

each $X_2$ independently is —O— or —N($R_4$)—;

each $R_4$ independently is hydrogen or $C_{1-6}$alkyl; and each $R_3$ independently is halogen or $C_{1-6}$alkyl;

in free base form or in acid addition salt form.

3. The therapeutic method of claim 1, further comprising administering a second cognition enhancer or a therapeutic compound useful for the treatment of cognitive impairments, psychotic and/or neurodegenerative disorders to the individual.

4. The therapeutic method according to claim 1, wherein the presence of (i) the CYP1A2 SNP rs2069514-A (SEQ ID NO.1), or (ii) the CYP1A2 SNP rs2069514-G (SEQ ID NO. 2), or (iii) a SNP forming a haplotype with said SNPs or a SNP in the same linkage disequilibrium with said SNPs is determined by using at least one oligonucleotide that specifically hybridizes with specific regions on the nucleic acid molecule carrying said SNP or SNPs.

5. The therapeutic method according to claim 4, wherein the presence of said SNPs is detected by sequence-specific primer (SSP) typing, sequence-specific oligonucleotide (SSO) typing, sequence based typing (SBT), DNA amplification such as polymerase chain reaction (PCR), microarray analysis, northern blot analysis, or reverse transcription PCR.

6. The therapeutic method of claim 2, wherein the alpha 7 nicotinic acetylcholine receptor activator of formula (I) is (R)-3-(6-p-tolyl-pyridin-3-yloxy)-1-aza-bicyclo[2.2.2]octane, in free base or acid addition salt form.

7. The therapeutic method of claim 6, wherein the alpha 7 nicotinic acetylcholine receptor activator of formula (I) is (R)-3-(6-p-tolyl-pyridin-3-yloxy)-1-aza-bicyclo[2.2.2]octane, in fumarate salt form.

8. The therapeutic method of claim 7, wherein the alpha 7 nicotinic acetylcholine receptor activator of formula (I) is (R)-3-(6-p-tolyl-pyridin-3-yloxy)-1-aza-bicyclo[2.2.2]octane, in mono-fumarate salt form.

9. The therapeutic method of claim 1, wherein the cognitive impairment, psychotic and/or neurodegenerative disorder is selected from the group consisting of: mild cognitive impairment, Alzheimer's disease, Parkinson's disease dementia, dementia with Lewy Bodies, vascular dementia, AIDS-dementia, senile dementia, mild cognitive impairment related to age (MCI), age associated memory impairment, autism, dementias in frontal lobe degenerations, stroke, basal ganglia degenerative disorders, multiple sclerosis, trauma, brain tumors, brain infections, hydrocephalus, depression, toxic or metabolic disorders and drug induced dementias.

10. The therapeutic method of claim 1, wherein the individual suffers from schizophrenia.

11. The therapeutic method of claim 9, wherein the individual suffers from schizophrenia.

* * * * *